(12) United States Patent
Kusleika (10) Patent No.: US 10,206,798 B2
(45) Date of Patent: *Feb. 19, 2019

(54) METHODS AND SYSTEMS FOR INCREASING A DENSITY OF A REGION OF A VASCULAR DEVICE

(71) Applicant: Covidien LP, Mansfield, MA (US)

(72) Inventor: Rich Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 15/268,669

(22) Filed: Sep. 19, 2016

(65) Prior Publication Data
US 2017/0000631 A1    Jan. 5, 2017

Related U.S. Application Data

(63) Continuation of application No. 13/664,854, filed on Oct. 31, 2012, now Pat. No. 9,452,070.

(51) Int. Cl.
*A61F 2/06* (2013.01)
*A61F 2/90* (2013.01)
(Continued)

(52) U.S. Cl.
CPC ............ *A61F 2/90* (2013.01); *A61F 2/852* (2013.01); *A61F 2/966* (2013.01); *A61F 2002/821* (2013.01); *A61F 2002/823* (2013.01)

(58) Field of Classification Search
CPC .... A61F 2/90; A61F 2/07; A61F 2/915; A61F 2/82; A61F 2/89; A61F 2/91; A61F 2/95;
(Continued)

(56) References Cited

U.S. PATENT DOCUMENTS

| 381,932 A | 5/1888 | Charles et al. |
| 2,919,467 A | 1/1960 | Mercer et al. |

(Continued)

FOREIGN PATENT DOCUMENTS

| CN | 101472537 A | 7/2009 |
| EP | 855170 A2 | 7/1998 |

(Continued)

OTHER PUBLICATIONS

Benndorf, et al., Treatment of a Ruptured Dissecting Vertebral Artery Aneurysm with Double Stent Placement: Case Report AJNR Am J Neuroradiol, Nov.-Dec. 2001, vol. 22, pp. 1844-1848.
(Continued)

*Primary Examiner* — David C Eastwood
*Assistant Examiner* — Mohamed G Gabr
(74) *Attorney, Agent, or Firm* — Fortem IP LLP; Matthew Lincicum (57) ABSTRACT

A vascular device is provided that includes a mesh structure formed of a plurality of spaced members. The structure has (i) a first, collapsed configuration, (ii) a second, expanded configuration, and (iii) a density of the plurality of members. The vascular device further includes an elastic member disposed along a region of the structure, the region having a proximal end and a distal end. The elastic member is configured to increase the density within the region by drawing at least one of the proximal and distal ends of the region toward the other of the proximal and distal ends when the structure is in the second configuration.

15 Claims, 7 Drawing Sheets

(51) Int. Cl.
*A61F 2/966* (2013.01)
*A61F 2/852* (2013.01)
*A61F 2/82* (2013.01)

(58) Field of Classification Search
CPC ...... A61F 2/88; A61F 2/01; A61F 2/06; A61F 2002/823; A61F 2002/075; A61F 2002/91558; A61F 2220/005; A61F 2250/0023; A61B 2017/00867; A61B 2017/1205; A61B 2017/12054; A61B 17/12118; A61B 17/12022; A61B 17/12; A61B 16/12109
See application file for complete search history.

(56) References Cited

U.S. PATENT DOCUMENTS

| | | |
|---|---|---|
| 4,321,711 A | 3/1982 | Mano |
| 4,503,569 A | 3/1985 | Dotter |
| 4,512,338 A | 4/1985 | Balko et al. |
| 4,538,622 A | 9/1985 | Samson et al. |
| 4,572,186 A | 2/1986 | Riggs et al. |
| 4,580,568 A | 4/1986 | Gianturco |
| 4,655,771 A | 4/1987 | Wallsten |
| 4,681,110 A | 7/1987 | Wiktor et al. |
| 4,733,665 A | 3/1988 | Palmaz et al. |
| 4,743,251 A | 5/1988 | Barra |
| 4,768,507 A | 9/1988 | Fischell et al. |
| 4,776,337 A | 10/1988 | Palmaz et al. |
| 4,856,516 A | 8/1989 | Hillstead et al. |
| 4,954,126 A | 9/1990 | Wallsten et al. |
| 5,011,488 A | 4/1991 | Ginsburg |
| 5,035,706 A | 7/1991 | Giantureo et al. |
| 5,041,126 A | 8/1991 | Gianturco |
| 5,061,275 A | 10/1991 | Wallsten et al. |
| 5,108,416 A | 4/1992 | Ryan et al. |
| 5,160,341 A | 11/1992 | Brenneman et al. |
| 5,180,368 A | 1/1993 | Garrison et al. |
| 5,192,297 A | 3/1993 | Hull |
| 5,197,978 A | 3/1993 | Hess |
| 5,201,757 A | 4/1993 | Heyn et al. |
| 5,209,731 A | 5/1993 | Sterman et al. |
| 5,242,399 A | 9/1993 | Hartigan et al. |
| 5,246,420 A | 9/1993 | Kraus et al. |
| 5,246,445 A | 9/1993 | Yachia et al. |
| 5,330,500 A | 7/1994 | Song et al. |
| 5,344,426 A | 9/1994 | Lau et al. |
| 5,360,443 A | 11/1994 | Barone et al. |
| 5,382,259 A | 1/1995 | Phelps et al. |
| 5,401,257 A | 3/1995 | Chevalier et al. |
| 5,405,377 A | 4/1995 | Cragg |
| 5,405,380 A | 4/1995 | Gianotti et al. |
| 5,415,637 A | 5/1995 | Khosravi |
| 5,421,826 A | 6/1995 | Crocker et al. |
| 5,423,849 A | 6/1995 | Samson et al. |
| 5,449,372 A | 9/1995 | Schmaltz et al. |
| 5,458,615 A | 10/1995 | Klemm et al. |
| 5,476,505 A | 12/1995 | Limon |
| 5,480,423 A | 1/1996 | Ravenscroft et al. |
| 5,484,444 A | 1/1996 | Braunschweiler et al. |
| 5,489,295 A | 2/1996 | Quiachon et al. |
| 5,507,767 A | 4/1996 | Maeda et al. |
| 5,507,768 A | 4/1996 | Lau et al. |
| 5,522,822 A | 6/1996 | Phelps et al. |
| 5,534,007 A | 7/1996 | St. Germain et al. |
| 5,545,208 A | 8/1996 | Hull et al. |
| 5,546,880 A | 8/1996 | Ronyak et al. |
| 5,549,662 A | 8/1996 | Fordenbacher |
| 5,562,641 A | 10/1996 | Flomenblit et al. |
| 5,562,728 A | 10/1996 | Sterman et al. |
| 5,591,225 A | 1/1997 | Okuda |
| 5,599,291 A | 2/1997 | Balbierz et al. |
| 5,601,593 A | 2/1997 | Freitag |
| 5,607,466 A | 3/1997 | Imbert et al. |
| 5,609,625 A | 3/1997 | Quiachon et al. |
| 5,626,602 A | 5/1997 | Gianotti et al. |
| 5,628,783 A | 5/1997 | Quiachon et al. |
| 5,628,788 A | 5/1997 | Pinchuk |
| 5,632,771 A | 5/1997 | Boatman et al. |
| 5,632,772 A | 5/1997 | Alcime et al. |
| 5,636,641 A | 6/1997 | Fariabi |
| 5,637,113 A * | 6/1997 | Tartaglia ............. A61F 2/07 604/104 |
| 5,639,278 A | 6/1997 | Dereume et al. |
| 5,645,559 A | 7/1997 | Laptewicz et al. |
| 5,667,522 A | 9/1997 | Flomenblit et al. |
| 5,674,276 A | 10/1997 | Strecker et al. |
| 5,683,451 A | 11/1997 | Evans et al. |
| 5,690,120 A | 11/1997 | Jacobsen et al. |
| 5,690,644 A | 11/1997 | Yurek et al. |
| 5,695,499 A | 12/1997 | Helgerson et al. |
| 5,700,269 A | 12/1997 | Pinchuk et al. |
| 5,702,418 A | 12/1997 | Ravenscroft et al. |
| 5,709,702 A | 1/1998 | Cogita |
| 5,709,703 A | 1/1998 | Lukic et al. |
| 5,718,159 A | 2/1998 | Thompson et al. |
| 5,725,570 A | 3/1998 | Heath et al. |
| 5,733,327 A | 3/1998 | Igaki et al. |
| 5,735,859 A | 4/1998 | Fischell et al. |
| 5,741,325 A | 4/1998 | Chaikof et al. |
| 5,741,333 A | 4/1998 | Frid et al. |
| 5,746,765 A | 5/1998 | Simon et al. |
| 5,749,883 A | 5/1998 | Halpern et al. |
| 5,749,920 A | 5/1998 | Quiachon et al. |
| 5,752,288 A | 5/1998 | Parkin et al. |
| 5,769,884 A | 6/1998 | Solovay |
| 5,769,885 A | 6/1998 | Quiachon et al. |
| 5,776,099 A | 7/1998 | Tremulis |
| 5,776,142 A | 7/1998 | Gunderson |
| 5,782,909 A | 7/1998 | Quiachon et al. |
| 5,797,952 A | 8/1998 | Klein |
| 5,800,518 A | 9/1998 | Quiachon et al. |
| 5,810,837 A | 9/1998 | Hofmann et al. |
| 5,817,102 A | 10/1998 | Johnson et al. |
| 5,817,105 A | 10/1998 | Van et al. |
| 5,824,039 A | 10/1998 | Quiachon et al. |
| 5,824,041 A | 10/1998 | Lenker et al. |
| 5,824,042 A | 10/1998 | Will et al. |
| 5,824,044 A | 10/1998 | Quiachon et al. |
| 5,824,058 A | 10/1998 | Ravenscroft et al. |
| 5,830,229 A | 11/1998 | Konya et al. |
| 5,833,632 A | 11/1998 | Jacobsen et al. |
| 5,836,868 A | 11/1998 | Resseman et al. |
| 5,843,168 A | 12/1998 | Dang |
| 5,868,754 A | 2/1999 | Levine et al. |
| 5,876,419 A | 3/1999 | Carpenter et al. |
| 5,888,201 A | 3/1999 | Stinson et al. |
| 5,902,266 A | 5/1999 | Leone et al. |
| 5,902,317 A | 5/1999 | Simon et al. |
| 5,906,640 A | 5/1999 | Penn et al. |
| 5,911,717 A | 6/1999 | Jacobsen et al. |
| 5,916,194 A | 6/1999 | Jacobsen et al. |
| 5,919,204 A | 7/1999 | Lukic et al. |
| 5,928,260 A | 7/1999 | Chin et al. |
| 5,944,728 A | 8/1999 | Bates et al. |
| 5,951,599 A | 9/1999 | Mccrory |
| 5,957,973 A | 9/1999 | Quiachon et al. |
| 5,957,974 A | 9/1999 | Thompson et al. |
| 5,964,797 A | 10/1999 | Ho |
| 5,980,530 A | 11/1999 | Willard et al. |
| 5,980,533 A | 11/1999 | Holman et al. |
| 5,984,957 A | 11/1999 | Laptewicz et al. |
| 6,012,277 A | 1/2000 | Prins et al. |
| 6,014,919 A | 1/2000 | Jacobsen et al. |
| 6,015,432 A | 1/2000 | Lund et al. |
| 6,017,319 A | 1/2000 | Jacobsen et al. |
| 6,019,778 A | 2/2000 | Wilson et al. |
| 6,019,786 A | 2/2000 | Thompson et al. |
| 6,022,369 A | 2/2000 | Lippert et al. |
| 6,024,754 A | 2/2000 | Engelson |
| 6,024,763 A | 2/2000 | Lenker et al. |
| 6,027,516 A | 2/2000 | Kolobow et al. |
| 6,033,436 A | 3/2000 | Steinke et al. |
| 6,039,721 A | 3/2000 | Johnson et al. |

(56) References Cited

U.S. PATENT DOCUMENTS

| | | | |
|---|---|---|---|
| 6,039,758 A | 3/2000 | Quiachon et al. |
| 6,042,589 A | 3/2000 | Marianne |
| 6,051,021 A | 4/2000 | Frid et al. |
| 6,056,993 A | 5/2000 | Leidner et al. |
| 6,063,111 A | 5/2000 | Hieshima et al. |
| 6,074,407 A | 6/2000 | Wallace et al. |
| 6,077,295 A | 6/2000 | Limon et al. |
| 6,080,191 A | 6/2000 | Summers |
| 6,083,257 A | 7/2000 | Woodroffe et al. |
| 6,093,199 A | 7/2000 | Brown et al. |
| 6,096,052 A | 8/2000 | Callister et al. |
| 6,102,942 A | 8/2000 | Ahari |
| 6,123,712 A | 9/2000 | Ellis et al. |
| 6,126,685 A | 10/2000 | Lenker et al. |
| 6,132,459 A | 10/2000 | Quiachon et al. |
| 6,139,543 A | 10/2000 | Esch et al. |
| 6,146,415 A | 11/2000 | Fitz |
| 6,149,680 A | 11/2000 | Shelso et al. |
| 6,159,228 A | 12/2000 | Frid et al. |
| 6,161,399 A | 12/2000 | Jayaraman |
| 6,165,194 A | 12/2000 | Denardo |
| 6,165,210 A | 12/2000 | Lau et al. |
| 6,165,213 A | 12/2000 | Goicoechea et al. |
| 6,168,592 B1 | 1/2001 | Kupiecki et al. |
| 6,174,330 B1 | 1/2001 | Stinson |
| 6,183,410 B1 | 2/2001 | Jacobsen et al. |
| 6,183,508 B1 | 2/2001 | Stinson et al. |
| 6,187,013 B1 | 2/2001 | Stoltze et al. |
| 6,193,708 B1 | 2/2001 | Ken et al. |
| 6,197,046 B1 | 3/2001 | Quiachon et al. |
| 6,203,569 B1 | 3/2001 | Wijay |
| 6,206,868 B1 | 3/2001 | Parodi et al. |
| 6,210,400 B1 | 4/2001 | Hebert et al. |
| 6,210,434 B1 | 4/2001 | Quiachon et al. |
| 6,210,435 B1 | 4/2001 | Quiachon et al. |
| 6,214,038 B1 | 4/2001 | Quiachon et al. |
| 6,214,042 B1 | 4/2001 | Jacobsen et al. |
| 6,221,102 B1 | 4/2001 | Baker et al. |
| 6,224,609 B1 | 5/2001 | Ressemann et al. |
| 6,224,829 B1 | 5/2001 | Piplani et al. |
| 6,231,598 B1 | 5/2001 | Berry et al. |
| 6,235,050 B1 | 5/2001 | Quiachon et al. |
| 6,241,759 B1 | 6/2001 | Quiachon et al. |
| 6,245,087 B1 | 6/2001 | Addis et al. |
| 6,245,103 B1 | 6/2001 | Stinson et al. |
| 6,251,132 B1 | 6/2001 | Ravenscroft et al. |
| 6,258,115 B1 | 7/2001 | Dubrul et al. |
| 6,260,458 B1 | 7/2001 | Jacobsen et al. |
| 6,261,305 B1 | 7/2001 | Marotta et al. |
| 6,261,316 B1 | 7/2001 | Shaolian et al. |
| 6,264,671 B1 | 7/2001 | Stack et al. |
| 6,264,689 B1 | 7/2001 | Dicarlo et al. |
| 6,270,523 B1 | 8/2001 | Herweck et al. |
| 6,280,465 B1 | 8/2001 | Cryer et al. |
| 6,283,991 B1 | 9/2001 | Cox et al. |
| 6,287,331 B1 | 9/2001 | Heath et al. |
| 6,287,333 B1 | 9/2001 | Appling et al. |
| 6,290,721 B1 | 9/2001 | Heath et al. |
| 6,299,636 B1 | 10/2001 | Schmitt et al. |
| 6,302,810 B2 | 10/2001 | Yokota et al. |
| 6,302,893 B1 | 10/2001 | Limon et al. |
| 6,309,353 B1 | 10/2001 | Itoh et al. |
| 6,322,576 B1 | 11/2001 | Wallace et al. |
| 6,322,586 B1 | 11/2001 | Monroe et al. |
| 6,322,587 B1 | 11/2001 | Johansson et al. |
| 6,325,826 B1 | 12/2001 | Vardi et al. |
| 6,334,871 B1 | 1/2002 | Loshakove et al. |
| 6,336,938 B1 | 1/2002 | Kavteladze et al. |
| 6,340,367 B1 | 1/2002 | Clerc et al. |
| 6,340,368 B1 | 1/2002 | Verbeek et al. |
| 6,342,068 B1 | 1/2002 | Thompson et al. |
| 6,344,041 B1 | 2/2002 | Kupiecki et al. |
| 6,348,063 B1 | 2/2002 | Yassour et al. |
| 6,350,199 B1 | 2/2002 | Williams et al. |
| 6,350,278 B1 | 2/2002 | Evans et al. |
| 6,355,051 B1 | 3/2002 | Sisskind et al. |
| 6,355,061 B1 | 3/2002 | Johansson et al. |
| 6,364,895 B1 | 4/2002 | Greenhalgh et al. |
| 6,368,339 B1 | 4/2002 | Amplatz et al. |
| 6,368,344 B1 | 4/2002 | Fitz et al. |
| 6,368,557 B1 | 4/2002 | Piplani et al. |
| 6,375,670 B1 | 4/2002 | Greenhalgh et al. |
| 6,375,676 B1 | 4/2002 | Cox et al. |
| 6,379,618 B1 | 4/2002 | Piplani et al. |
| 6,380,457 B1 | 4/2002 | Yurek et al. |
| 6,389,946 B1 | 5/2002 | Frid et al. |
| 6,395,017 B1 | 5/2002 | Dwyer et al. |
| 6,395,021 B1 | 5/2002 | Hart et al. |
| 6,395,022 B1 | 5/2002 | Quiachon et al. |
| 6,398,802 B1 | 6/2002 | Yee |
| 6,409,683 B1 | 6/2002 | Fonseca et al. |
| 6,413,235 B1 | 7/2002 | Parodi et al. |
| 6,416,519 B1 | 7/2002 | Vandusseldorp et al. |
| 6,416,536 B1 | 7/2002 | Yee et al. |
| 6,419,693 B1 | 7/2002 | Fariabi et al. |
| 6,428,221 B1 | 8/2002 | Dolce et al. |
| 6,428,489 B1 | 8/2002 | Jacobsen et al. |
| 6,440,088 B1 | 8/2002 | Jacobsen et al. |
| 6,443,971 B1 | 9/2002 | Boylan et al. |
| 6,443,979 B1 | 9/2002 | Stalker et al. |
| 6,454,999 B1 | 9/2002 | Farhangnia et al. |
| 6,468,301 B1 | 10/2002 | Amplatz et al. |
| 6,477,768 B1 | 11/2002 | Wildner |
| 6,478,778 B1 | 11/2002 | Jacobsen et al. |
| 6,482,221 B1 | 11/2002 | Hebert et al. |
| 6,488,705 B2 | 12/2002 | Schmitt et al. |
| 6,491,648 B1 | 12/2002 | Cornish et al. |
| 6,494,895 B2 | 12/2002 | Addis et al. |
| 6,497,711 B1 | 12/2002 | Barry et al. |
| 6,503,450 B1 | 1/2003 | Afzal et al. |
| 6,514,261 B1 | 2/2003 | Randall et al. |
| 6,514,285 B1 | 2/2003 | Pinchasik et al. |
| 6,524,299 B1 | 2/2003 | Tran et al. |
| 6,527,763 B2 | 3/2003 | Esch et al. |
| 6,533,811 B1 | 3/2003 | Ryan et al. |
| 6,540,778 B1 | 4/2003 | Quiachon et al. |
| 6,547,779 B2 | 4/2003 | Levine et al. |
| 6,551,352 B2 * | 4/2003 | Clerc ................... A61F 2/90 156/143 |
| 6,572,646 B1 | 6/2003 | Boylan et al. |
| 6,576,006 B2 | 6/2003 | Limon et al. |
| 6,582,460 B1 | 6/2003 | Cryer et al. |
| 6,582,461 B1 | 6/2003 | Burmeister et al. |
| 6,589,273 B1 | 7/2003 | Mcdermott et al. |
| 6,592,616 B1 | 7/2003 | Stack et al. |
| 6,595,989 B1 | 7/2003 | Schaer et al. |
| 6,602,271 B2 | 8/2003 | Adams et al. |
| 6,602,280 B2 | 8/2003 | Chobotov |
| 6,605,110 B2 | 8/2003 | Harrison et al. |
| 6,613,075 B1 | 9/2003 | Healy et al. |
| 6,613,078 B1 | 9/2003 | Barone et al. |
| 6,622,604 B1 | 9/2003 | Peiffer et al. |
| 6,623,518 B2 | 9/2003 | Thompson et al. |
| 6,635,068 B1 | 10/2003 | Dubrul et al. |
| 6,638,243 B2 | 10/2003 | Kupiecki et al. |
| 6,645,240 B2 | 11/2003 | Yee et al. |
| 6,646,218 B1 | 11/2003 | Campbell et al. |
| 6,652,508 B2 | 11/2003 | Griffin et al. |
| 6,652,574 B1 | 11/2003 | Jayaraman |
| 6,656,212 B2 | 12/2003 | Ravenscroft et al. |
| 6,656,218 B1 | 12/2003 | Denardo et al. |
| 6,660,024 B1 | 12/2003 | Chang et al. |
| 6,660,032 B2 | 12/2003 | Klumb et al. |
| 6,663,666 B1 | 12/2003 | Quiachon et al. |
| 6,666,881 B1 | 12/2003 | Richter |
| 6,669,719 B2 | 12/2003 | Brenneman et al. |
| 6,673,089 B1 | 1/2004 | Yassour et al. |
| 6,673,100 B2 | 1/2004 | Mitelberg et al. |
| 6,679,893 B1 | 1/2004 | Tran et al. |
| 6,682,557 B1 | 1/2004 | Quiachon et al. |
| 6,689,120 B1 | 2/2004 | Gerdts et al. |
| 6,689,162 B1 | 2/2004 | Thompson et al. |
| 6,699,274 B2 | 3/2004 | Stinson et al. |
| 6,702,843 B1 | 3/2004 | Brown et al. |

(56) References Cited

U.S. PATENT DOCUMENTS

| | | |
|---|---|---|
| 6,709,454 B1 | 3/2004 | Cox et al. |
| 6,712,834 B2 | 3/2004 | Yassour et al. |
| 6,726,700 B1 | 4/2004 | Levine et al. |
| 6,733,519 B2 | 5/2004 | Lashinski et al. |
| 6,740,105 B2 | 5/2004 | Yodfat et al. |
| 6,740,112 B2 | 5/2004 | Yodfat et al. |
| 6,743,219 B1 | 6/2004 | Dwyer et al. |
| 6,755,855 B2 | 6/2004 | Yurek et al. |
| 6,758,885 B2 | 7/2004 | Leffel et al. |
| 6,767,361 B2 | 7/2004 | Quiachon et al. |
| 6,773,446 B1 | 8/2004 | Dwyer et al. |
| 6,793,667 B2 | 9/2004 | Hebert et al. |
| 6,814,746 B2 | 11/2004 | Thompson et al. |
| 6,814,748 B1 | 11/2004 | Baker et al. |
| 6,818,006 B2 | 11/2004 | Douk et al. |
| 6,833,003 B2 | 12/2004 | Jones et al. |
| 6,849,084 B2 | 2/2005 | Rabkin et al. |
| 6,858,034 B1 | 2/2005 | Hijlkema et al. |
| 6,860,893 B2 | 3/2005 | Wallace et al. |
| 6,860,898 B2 | 3/2005 | Stack et al. |
| 6,860,899 B1 | 3/2005 | Rivelli et al. |
| 6,860,900 B2 | 3/2005 | Clerc et al. |
| 6,860,901 B1 | 3/2005 | Baker et al. |
| 6,865,735 B1 | 3/2005 | Sirer et al. |
| 6,866,677 B2 | 3/2005 | Douk et al. |
| 6,866,679 B2 | 3/2005 | Kusleika et al. |
| 6,866,680 B2 | 3/2005 | Yassour et al. |
| 6,881,221 B2 | 4/2005 | Golds et al. |
| 6,887,267 B2 | 5/2005 | Dworschak et al. |
| 6,890,337 B2 | 5/2005 | Feeser et al. |
| 6,893,451 B2 | 5/2005 | Cano et al. |
| 6,918,921 B2 | 7/2005 | Brady et al. |
| 6,932,837 B2 | 8/2005 | Amplatz et al. |
| 6,936,055 B1 | 8/2005 | Ken et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,964,672 B2 | 11/2005 | Brady et al. |
| 6,969,396 B2 | 11/2005 | Krolik et al. |
| 6,976,991 B2 | 12/2005 | Hebert et al. |
| 6,989,024 B2 | 1/2006 | Hebert et al. |
| 6,994,721 B2 | 2/2006 | Israel et al. |
| 7,001,422 B2 | 2/2006 | Escamilla et al. |
| 7,004,962 B2 | 2/2006 | Stinson et al. |
| 7,004,964 B2 | 2/2006 | Thompson et al. |
| 7,011,675 B2 | 3/2006 | Hemerick et al. |
| 7,037,330 B1 | 5/2006 | Donahue et al. |
| 7,041,129 B2 | 5/2006 | Yang et al. |
| 7,066,951 B2 | 6/2006 | Chobotov et al. |
| 7,069,835 B2 | 7/2006 | Nishri et al. |
| 7,074,236 B2 | 7/2006 | Rabkin et al. |
| 7,093,527 B2 | 8/2006 | Nishri et al. |
| 7,101,392 B2 | 9/2006 | Heath et al. |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,137,990 B2 | 11/2006 | Hebert et al. |
| 7,166,125 B1 | 1/2007 | Baker et al. |
| 7,169,170 B2 | 1/2007 | Widenhouse et al. |
| 7,169,172 B2 | 1/2007 | Levine et al. |
| 7,172,617 B2 | 2/2007 | Dimatteo et al. |
| 7,192,434 B2 | 3/2007 | Anderson et al. |
| 7,195,639 B2 | 3/2007 | Quiachon et al. |
| 7,195,648 B2 | 3/2007 | Mitelberg et al. |
| 7,201,768 B2 | 4/2007 | Mitelberg et al. |
| 7,201,769 B2 | 4/2007 | Jones et al. |
| 7,211,109 B2 | 5/2007 | Thompson et al. |
| 7,213,495 B2 | 5/2007 | Mccullagh et al. |
| 7,220,271 B2 | 5/2007 | Clubb et al. |
| 7,235,096 B1 | 6/2007 | Van Tassel et al. |
| 7,264,632 B2 | 9/2007 | Wright et al. |
| 7,275,471 B2 | 10/2007 | Nishri et al. |
| 7,279,005 B2 | 10/2007 | Stinson et al. |
| 7,279,208 B1 | 10/2007 | Goffena et al. |
| 7,294,137 B2 | 11/2007 | Rivelli et al. |
| 7,294,146 B2 | 11/2007 | Chew et al. |
| 7,300,456 B2 | 11/2007 | Grainger et al. |
| 7,300,460 B2 | 11/2007 | Levine et al. |
| 7,306,624 B2 | 12/2007 | Yodfat et al. |
| 7,309,351 B2 | 12/2007 | Escamilla et al. |
| 7,311,031 B2 | 12/2007 | Mccullagh et al. |
| 7,320,702 B2 | 1/2008 | Karat et al. |
| 7,323,001 B2 | 1/2008 | Clubb et al. |
| 7,331,973 B2 | 2/2008 | Gesswein et al. |
| 7,331,976 B2 | 2/2008 | Mcguckin et al. |
| 7,331,985 B2 | 2/2008 | Thompson et al. |
| 7,338,518 B2 | 3/2008 | Chobotov et al. |
| 7,438,712 B2 | 10/2008 | Chouinard et al. |
| 7,462,192 B2 | 12/2008 | Clerc et al. |
| 7,468,070 B2 | 12/2008 | Henry et al. |
| 7,470,282 B2 | 12/2008 | Shelso et al. |
| 7,473,271 B2 | 1/2009 | Gunderson et al. |
| 7,491,224 B2 | 2/2009 | Cox et al. |
| 7,520,893 B2 | 4/2009 | Rivelli et al. |
| RE40,816 E | 6/2009 | Taylor et al. |
| 7,572,288 B2 | 8/2009 | Cox et al. |
| 7,572,290 B2 | 8/2009 | Yodfat et al. |
| 7,588,597 B2 | 9/2009 | Frid |
| 7,695,507 B2 | 4/2010 | Donahue et al. |
| 7,763,011 B2 | 7/2010 | Ortiz et al. |
| 7,771,463 B2 | 8/2010 | Ton et al. |
| 7,854,760 B2 | 12/2010 | Henry et al. |
| 7,901,447 B2 | 3/2011 | Correa et al. |
| 7,942,925 B2 | 5/2011 | Yodfat et al. |
| 8,007,529 B2 | 8/2011 | Yan et al. |
| 8,092,486 B2 | 1/2012 | Berrada et al. |
| 8,092,508 B2 | 1/2012 | Leynov et al. |
| 8,192,484 B2 | 6/2012 | Frid |
| 8,382,825 B2 | 2/2013 | Garcia et al. |
| 8,394,119 B2 | 3/2013 | Carion et al. |
| 8,398,701 B2 | 3/2013 | Tran et al. |
| 8,617,234 B2 | 12/2013 | Garcia et al. |
| 8,623,067 B2 | 1/2014 | Tran et al. |
| 8,628,564 B2 | 1/2014 | Tran et al. |
| 8,764,817 B2 | 7/2014 | Sheldon et al. |
| 8,801,772 B2 | 8/2014 | Shobayashi et al. |
| 8,979,918 B2 | 3/2015 | Murayama |
| 9,050,205 B2 | 6/2015 | Tran et al. |
| 9,114,001 B2 | 8/2015 | Kusleika et al. |
| 9,157,174 B2 | 10/2015 | Kusleika et al. |
| 9,452,070 B2 | 9/2016 | Kusleika et al. |
| 9,509,586 B2 | 11/2016 | Damodaran et al. |
| 2001/0027338 A1 | 10/2001 | Greenberg et al. |
| 2001/0044651 A1 | 11/2001 | Steinke et al. |
| 2001/0049547 A1 | 12/2001 | Moore et al. |
| 2001/0056299 A1 | 12/2001 | Thompson et al. |
| 2002/0004667 A1 | 1/2002 | Adams et al. |
| 2002/0007194 A1 | 1/2002 | Plowiecki et al. |
| 2002/0029061 A1 | 3/2002 | Amplatz et al. |
| 2002/0035396 A1 | 3/2002 | Heath et al. |
| 2002/0062091 A1 | 5/2002 | Jacobsen et al. |
| 2002/0078808 A1 | 6/2002 | Jacobsen et al. |
| 2002/0082558 A1 | 6/2002 | Samson et al. |
| 2002/0087119 A1 | 7/2002 | Parodi et al. |
| 2002/0111633 A1 | 8/2002 | Stoltze et al. |
| 2002/0111648 A1 | 8/2002 | Kusleika et al. |
| 2002/0120323 A1 | 8/2002 | Thompson et al. |
| 2002/0138133 A1 | 9/2002 | Lenz et al. |
| 2002/0143361 A1 | 10/2002 | Douk et al. |
| 2002/0143384 A1 | 10/2002 | Ozasa et al. |
| 2002/0169473 A1 | 11/2002 | Sepetka et al. |
| 2002/0169474 A1 | 11/2002 | Kusleika et al. |
| 2002/0173839 A1 | 11/2002 | Leopold et al. |
| 2002/0188314 A1 | 12/2002 | Anderson et al. |
| 2002/0193864 A1 | 12/2002 | Khosravi et al. |
| 2003/0009215 A1 | 1/2003 | Mayer et al. |
| 2003/0023299 A1 | 1/2003 | Amplatz et al. |
| 2003/0069522 A1 | 4/2003 | Jacobsen et al. |
| 2003/0100945 A1 | 5/2003 | Yodfat et al. |
| 2003/0130684 A1 | 7/2003 | Brady et al. |
| 2003/0135258 A1 | 7/2003 | Andreas et al. |
| 2003/0163155 A1 | 8/2003 | Haverkost et al. |
| 2003/0163156 A1 | 8/2003 | Hebert et al. |

(56) References Cited

U.S. PATENT DOCUMENTS

| | | |
|---|---|---|
| 2003/0176884 A1 | 9/2003 | Berrada et al. |
| 2003/0187495 A1 | 10/2003 | Cully et al. |
| 2003/0212429 A1 | 11/2003 | Keegan et al. |
| 2003/0212430 A1 | 11/2003 | Bose et al. |
| 2004/0024416 A1 | 2/2004 | Yodfat et al. |
| 2004/0030265 A1 | 2/2004 | Murayama et al. |
| 2004/0044395 A1 | 3/2004 | Nelson et al. |
| 2004/0073300 A1 | 4/2004 | Chouinard et al. |
| 2004/0088037 A1 | 5/2004 | Nachreiner et al. |
| 2004/0093010 A1 | 5/2004 | Gesswein et al. |
| 2004/0098099 A1 | 5/2004 | Mccullagh et al. |
| 2004/0133223 A1 | 7/2004 | Weber et al. |
| 2004/0153117 A1 | 8/2004 | Clubb et al. |
| 2004/0162606 A1 | 8/2004 | Thompson et al. |
| 2004/0172055 A1 | 9/2004 | Huter et al. |
| 2004/0186368 A1 | 9/2004 | Ramzipoor et al. |
| 2004/0193178 A1 | 9/2004 | Nikolchev et al. |
| 2004/0193179 A1 | 9/2004 | Nikolchev et al. |
| 2004/0193208 A1 | 9/2004 | Talpade et al. |
| 2004/0199243 A1 | 10/2004 | Yodfat et al. |
| 2004/0210235 A1 | 10/2004 | Deshmukh et al. |
| 2004/0215332 A1 | 10/2004 | Frid et al. |
| 2004/0220585 A1 | 11/2004 | Nikolchev et al. |
| 2004/0220608 A1 | 11/2004 | D'aquanni et al. |
| 2004/0220663 A1 | 11/2004 | Rivelli et al. |
| 2004/0254628 A1 | 12/2004 | Nazzaro et al. |
| 2004/0260331 A1 | 12/2004 | D'aquanni et al. |
| 2005/0004595 A1 | 1/2005 | Boyle et al. |
| 2005/0021075 A1 | 1/2005 | Bonnette et al. |
| 2005/0033407 A1 | 2/2005 | Weber et al. |
| 2005/0038447 A1 | 2/2005 | Huffmaster et al. |
| 2005/0051243 A1 | 3/2005 | Forbes et al. |
| 2005/0055047 A1 | 3/2005 | Greenhalgh et al. |
| 2005/0059889 A1 | 3/2005 | Mayer et al. |
| 2005/0060017 A1 | 3/2005 | Fischell et al. |
| 2005/0090888 A1 | 4/2005 | Hines et al. |
| 2005/0101989 A1 | 5/2005 | Cully et al. |
| 2005/0137680 A1 | 6/2005 | Ortiz et al. |
| 2005/0149111 A1 | 7/2005 | Kanazawa et al. |
| 2005/0165441 A1 | 7/2005 | Mcguckin et al. |
| 2005/0177186 A1 | 8/2005 | Cully et al. |
| 2005/0192620 A1 | 9/2005 | Cully et al. |
| 2005/0197689 A1 | 9/2005 | Molaei et al. |
| 2005/0209672 A1 | 9/2005 | George et al. |
| 2005/0209678 A1 | 9/2005 | Henkes et al. |
| 2005/0246010 A1 | 11/2005 | Alexander et al. |
| 2005/0267568 A1 | 12/2005 | Berez et al. |
| 2005/0283220 A1 | 12/2005 | Gobran et al. |
| 2005/0288764 A1 | 12/2005 | Snow et al. |
| 2005/0288766 A1 | 12/2005 | Plain et al. |
| 2006/0020324 A1 | 1/2006 | Schmid et al. |
| 2006/0036309 A1 | 2/2006 | Hebert et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116713 A1 | 6/2006 | Sepetka et al. |
| 2006/0116750 A1 | 6/2006 | Hebert et al. |
| 2006/0184238 A1 | 8/2006 | Kaufmann et al. |
| 2006/0195118 A1 | 8/2006 | Richardson et al. |
| 2006/0206148 A1 | 9/2006 | Khairkhahan et al. |
| 2006/0206200 A1 | 9/2006 | Garcia et al. |
| 2006/0206201 A1 | 9/2006 | Garci et al. |
| 2006/0212127 A1 | 9/2006 | Karabey et al. |
| 2006/0271149 A1 | 11/2006 | Berez et al. |
| 2006/0271153 A1 | 11/2006 | Garcia et al. |
| 2006/0276910 A1 | 12/2006 | Weber et al. |
| 2007/0021816 A1 | 1/2007 | Rudin et al. |
| 2007/0043419 A1 | 2/2007 | Nikolchev et al. |
| 2007/0055365 A1 | 3/2007 | Greenberg et al. |
| 2007/0060994 A1 | 3/2007 | Gobran et al. |
| 2007/0073379 A1 | 3/2007 | Chang et al. |
| 2007/0077347 A1 | 4/2007 | Richter et al. |
| 2007/0100321 A1 | 5/2007 | Rudakov et al. |
| 2007/0100414 A1 | 5/2007 | Licata et al. |
| 2007/0100430 A1 | 5/2007 | Rudakov et al. |
| 2007/0112415 A1 | 5/2007 | Bartlett et al. |
| 2007/0119295 A1 | 5/2007 | Mccullagh et al. |
| 2007/0123969 A1 | 5/2007 | Gianotti et al. |
| 2007/0162104 A1 | 7/2007 | Frid et al. |
| 2007/0167980 A1 | 7/2007 | Figulla et al. |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0208367 A1 | 9/2007 | Fiorella et al. |
| 2007/0208373 A1 | 9/2007 | Zaver et al. |
| 2007/0208376 A1 | 9/2007 | Meng et al. |
| 2007/0208415 A1 | 9/2007 | Grotheim et al. |
| 2007/0219619 A1 | 9/2007 | Dieck et al. |
| 2007/0225760 A1 | 9/2007 | Moszner et al. |
| 2007/0233175 A1 | 10/2007 | Zaver et al. |
| 2007/0239261 A1 | 10/2007 | Bose et al. |
| 2007/0255386 A1 | 11/2007 | Tenne et al. |
| 2007/0255388 A1 | 11/2007 | Rudakov et al. |
| 2007/0280850 A1 | 12/2007 | Carlson et al. |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0005898 A1 | 1/2008 | Nishida et al. |
| 2008/0015673 A1 | 1/2008 | Chuter et al. |
| 2008/0033341 A1 | 2/2008 | Grad et al. |
| 2008/0033526 A1 | 2/2008 | Atladottir et al. |
| 2008/0039930 A1 | 2/2008 | Jones et al. |
| 2008/0039933 A1 | 2/2008 | Yodfat et al. |
| 2008/0071351 A1 | 3/2008 | Flanagan et al. |
| 2008/0082154 A1 | 4/2008 | Tseng et al. |
| 2008/0114391 A1 | 5/2008 | Dieck et al. |
| 2008/0119943 A1 | 5/2008 | Armstrong et al. |
| 2008/0125855 A1 | 5/2008 | Henkes et al. |
| 2008/0208320 A1 | 8/2008 | Tan-Malecki et al. |
| 2008/0221666 A1 | 9/2008 | Licata et al. |
| 2008/0221670 A1 | 9/2008 | Clerc et al. |
| 2008/0221671 A1 | 9/2008 | Chouinard et al. |
| 2008/0255654 A1 | 10/2008 | Hebert et al. |
| 2008/0255655 A1 | 10/2008 | Kusleika et al. |
| 2008/0262590 A1 | 10/2008 | Murray et al. |
| 2008/0269774 A1 | 10/2008 | Garcia et al. |
| 2008/0275497 A1 | 11/2008 | Palmer et al. |
| 2008/0275498 A1 | 11/2008 | Palmer et al. |
| 2008/0294104 A1 | 11/2008 | Mawad et al. |
| 2008/0300667 A1 | 12/2008 | Hebert et al. |
| 2008/0300668 A1 | 12/2008 | Bonsignore et al. |
| 2008/0300673 A1 | 12/2008 | Clerc et al. |
| 2009/0024202 A1 | 1/2009 | Dave et al. |
| 2009/0024205 A1 | 1/2009 | Hebert et al. |
| 2009/0030496 A1 | 1/2009 | Kaufmann et al. |
| 2009/0030497 A1 | 1/2009 | Metcalf et al. |
| 2009/0054981 A1 | 2/2009 | Frid et al. |
| 2009/0099643 A1 | 4/2009 | Hyodoh et al. |
| 2009/0105802 A1 | 4/2009 | Henry et al. |
| 2009/0105803 A1 | 4/2009 | Shelso et al. |
| 2009/0125093 A1 | 5/2009 | Hansen et al. |
| 2009/0192536 A1 | 7/2009 | Berez et al. |
| 2009/0192587 A1 | 7/2009 | Frid et al. |
| 2009/0198318 A1 | 8/2009 | Berez et al. |
| 2009/0222035 A1 | 9/2009 | Schneiderman et al. |
| 2009/0270974 A1 | 10/2009 | Berez et al. |
| 2009/0287241 A1 | 11/2009 | Berez et al. |
| 2009/0287288 A1* | 11/2009 | Berez ............... A61F 2/844 623/1.2 |
| 2009/0288000 A1 | 11/2009 | Mcpherson et al. |
| 2009/0292348 A1 | 11/2009 | Berez et al. |
| 2009/0318947 A1 | 12/2009 | Garcia et al. |
| 2009/0319017 A1 | 12/2009 | Berez et al. |
| 2010/0010624 A1 | 1/2010 | Berez et al. |
| 2010/0042200 A1 | 2/2010 | Richter et al. |
| 2010/0061604 A1 | 3/2010 | Nahm et al. |
| 2010/0063531 A1 | 3/2010 | Rudakov et al. |
| 2010/0070024 A1 | 3/2010 | Venturelli et al. |
| 2010/0076317 A1 | 3/2010 | Babic et al. |
| 2010/0152834 A1 | 6/2010 | Hannes et al. |
| 2010/0161025 A1 | 6/2010 | Kuppurathanam et al. |
| 2010/0174269 A1 | 7/2010 | Tompkins et al. |
| 2010/0174309 A1 | 7/2010 | Fulkerson et al. |
| 2010/0179583 A1 | 7/2010 | Carpenter et al. |

(56) References Cited

U.S. PATENT DOCUMENTS

| | | |
|---|---|---|
| 2010/0179647 A1 | 7/2010 | Carpenter et al. |
| 2010/0198334 A1 | 8/2010 | Yodfat et al. |
| 2010/0204779 A1 | 8/2010 | Schuessler et al. |
| 2010/0211154 A1 | 8/2010 | Murayama et al. |
| 2010/0222864 A1 | 9/2010 | Rivelli et al. |
| 2010/0241214 A1 | 9/2010 | Holzer et al. |
| 2010/0256732 A1 | 10/2010 | Shin et al. |
| 2010/0256733 A1 | 10/2010 | Schuessler et al. |
| 2010/0280587 A1 | 11/2010 | Ortiz et al. |
| 2010/0318174 A1 | 12/2010 | Shaolian et al. |
| 2010/0318178 A1 | 12/2010 | Rapaport et al. |
| 2011/0016427 A1 | 1/2011 | Douen et al. |
| 2011/0040372 A1 | 2/2011 | Hansen et al. |
| 2011/0046718 A1 | 2/2011 | Cattaneo et al. |
| 2011/0046720 A1 | 2/2011 | Shalev et al. |
| 2011/0054589 A1 | 3/2011 | Bashiri et al. |
| 2011/0134663 A1 | 6/2011 | Sakakibara |
| 2011/0166592 A1 | 7/2011 | Garcia et al. |
| 2011/0166637 A1 | 7/2011 | Irwin et al. |
| 2011/0166639 A1 | 7/2011 | Pulnev et al. |
| 2011/0179389 A1 | 7/2011 | Douen et al. |
| 2011/0184451 A1 | 7/2011 | Sahl et al. |
| 2011/0190862 A1 | 8/2011 | Bashiri et al. |
| 2011/0245862 A1 | 10/2011 | Dieck et al. |
| 2011/0270178 A1 | 11/2011 | Fiorella et al. |
| 2012/0035643 A1 | 2/2012 | Khairkhahan et al. |
| 2012/0041459 A1 | 2/2012 | Fiorella et al. |
| 2012/0158124 A1 | 6/2012 | Zaver et al. |
| 2012/0253454 A1 | 10/2012 | Costello et al. |
| 2012/0290067 A1 | 11/2012 | Cam et al. |
| 2012/0316638 A1 | 12/2012 | Grad et al. |
| 2012/0323309 A1 | 12/2012 | Cattaneo et al. |
| 2013/0116773 A1 | 5/2013 | Roeder et al. |
| 2013/0123901 A1 | 5/2013 | Connor et al. |
| 2013/0138202 A1 | 5/2013 | Paul et al. |
| 2013/0172975 A1 | 7/2013 | Berez et al. |
| 2013/0190856 A1 | 7/2013 | Von Oepen et al. |
| 2013/0204347 A1 | 8/2013 | Armstrong et al. |
| 2013/0211489 A1 | 8/2013 | Makower et al. |
| 2013/0211497 A1 | 8/2013 | Charlebois et al. |
| 2013/0274849 A1 | 10/2013 | Zaver et al. |
| 2014/0018843 A1 | 1/2014 | Berez et al. |
| 2014/0074149 A1 | 3/2014 | Garcia et al. |
| 2014/0114342 A1 | 4/2014 | Berez et al. |
| 2014/0121744 A1 | 5/2014 | Kusleika et al. |
| 2014/0121745 A1 | 5/2014 | Kusleika et al. |
| 2014/0121746 A1 | 5/2014 | Kusleika et al. |
| 2014/0128957 A1 | 5/2014 | Losordo et al. |
| 2014/0222130 A1 | 8/2014 | Kusleika et al. |
| 2014/0316454 A1 | 10/2014 | Zaver et al. |
| 2014/0336741 A1 | 11/2014 | Janjua et al. |
| 2015/0359646 A1 | 12/2015 | Kusleika et al. |

FOREIGN PATENT DOCUMENTS

| | | |
|---|---|---|
| EP | 1683541 A2 | 7/2006 |
| EP | 1942972 A1 | 7/2008 |
| EP | 1872742 B1 | 5/2009 |
| EP | 2078512 A1 | 7/2009 |
| FR | 2556210 A1 | 6/1985 |
| JP | 10328216 A | 12/1998 |
| JP | 11506686 A | 6/1999 |
| JP | 11299901 A | 11/1999 |
| JP | 2001509412 A | 7/2001 |
| JP | 2002253682 A | 9/2002 |
| JP | 2003520103 A | 7/2003 |
| JP | 2004049585 A | 2/2004 |
| JP | 2005074230 A | 3/2005 |
| JP | 2006506201 A | 2/2006 |
| JP | 2008541832 A | 11/2008 |
| JP | 4673987 B2 | 4/2011 |
| WO | 8800813 A1 | 2/1988 |
| WO | 9532757 A1 | 12/1995 |
| WO | 9804211 A1 | 2/1998 |
| WO | 9847447 A1 | 10/1998 |
| WO | 9902092 A1 | 1/1999 |
| WO | 9905977 A1 | 2/1999 |
| WO | 9949812 A3 | 12/1999 |
| WO | 0105331 A1 | 1/2001 |
| WO | 0152771 A1 | 7/2001 |
| WO | 0205729 A2 | 1/2002 |
| WO | 0247579 A1 | 6/2002 |
| WO | 02054988 A3 | 1/2003 |
| WO | 03007840 A2 | 1/2003 |
| WO | 03043527 A2 | 5/2003 |
| WO | 03049600 A2 | 6/2003 |
| WO | 03057079 A1 | 7/2003 |
| WO | 03073963 A2 | 9/2003 |
| WO | 2004087006 A3 | 11/2004 |
| WO | 2005021061 A2 | 3/2005 |
| WO | 2005023149 A3 | 12/2005 |
| WO | 2006034140 A2 | 3/2006 |
| WO | 2006073745 A2 | 7/2006 |
| WO | 2006127005 A1 | 11/2006 |
| WO | 2007122396 A1 | 11/2007 |
| WO | 2008005898 A2 | 1/2008 |
| WO | 2007139689 A3 | 9/2008 |
| WO | 2007139699 A3 | 9/2008 |
| WO | 2008156683 A1 | 12/2008 |
| WO | 2005115118 A3 | 7/2009 |
| WO | 2009105710 A1 | 8/2009 |
| WO | 2010127838 A2 | 11/2010 |
| WO | 2011023105 A1 | 3/2011 |

OTHER PUBLICATIONS

Brilstra, et al., Treatment of Intracranial Aneurysms by Embolization with Coils: A Systematic Review, Stroke, Journal of the American Heart Assocation, 1999, vol. 30, pp. 470-476.

Ferguson, Physical Factors in the Initiation, Growth and Rupture of Human Intracranial Saccular Ameurysms, J. Neurosurg, Dec. 1972, vol. 37, pp. 666-667.

Geremia, et al., Embolization of Experimentally Created Aneurysms with Intravascular Stent Devices, ANJR American Journal of Neuroradiology, Aug. 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosity, Ann of Biomedical Eng., 1997, vol. 25, pp. 460-469, Buffaly, NY.

Lieber, et al., The Physics of Endoluminal Stenting in the Treatment of Cerebrovascular Aneurysms, Neurological Research, 2002, Vcol 24, Issue Supplement 1, pp. S32-S42.

Moss, et al., Vascular Occlusion with a Balloon-Expadable Stent Occluder, Radiology, May 1994, vol. 191, Issue 2, pp. 483-486.

Pereira, History of Endovascular Aneurysm Occlusion, Management of Cerebral Aneurysms, 2004, pp. 11-26.

Qureshi, Endovascular Treatment of Cerebrovascular Diseases and Intracranial Neoplasms, The lancelet, Mar. 2004, vol. 363, pp. 804-813.

Steiger, Pathophysiology of Development and Rupture of Cerebral Aneurysms, Acta Nurochirugica, Mar. 1999, vol. Supplemetum 48, Pages in 62 pages.

Tenaglia, et al., Ultrasound Guide Wire-Directed Stent Deployment, Duke University Medical Center, Department of Medicine, 1993 USA.

Yu, et al., A Steady Flow Analysis on the Stented and Non-Stented Sidewall Aneurysm Models, Medical Engineering and Physics, Apr. 1999, Issue 21, pp. 133-141.

* cited by examiner

METHODS AND SYSTEMS FOR INCREASING A DENSITY OF A REGION OF A VASCULAR DEVICE

CROSS-REFERENCE TO RELATED APPLICATION

The present application is a continuation of U.S. patent application Ser. No. 13/664,854, filed Oct. 31, 2012, the disclosure of which is incorporated herein by reference in its entirety.

BACKGROUND

Lumens in a patient's body can change in size, shape, and/or patency, and such changes can present complications or affect associated bodily functions. For example, the walls of the vasculature, particularly arterial walls, may develop a pathological dilatation, commonly called an aneurysm. Aneurysms are observed as a ballooning-out of the wall of an artery. This is a result of the vessel wall being weakened by disease, injury, or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but an aneurysm can have serious health consequences such as a stroke if one should rupture in the brain. Additionally, a ruptured aneurysm can also result in death.

SUMMARY

The subject technology is illustrated, for example, according to various aspects described below. Various examples of aspects of the subject technology are described as numbered clauses (1, 2, 3, etc.) for convenience. These are provided as examples, and do not limit the subject technology. It is noted that any of the dependent clauses may be combined in any combination, and placed into a respective independent clause, e.g., clause 1 and 21. The other clauses can be presented in a similar manner.

A vascular device, comprising:
a mesh structure formed of a plurality of spaced members, the structure having (i) a first, collapsed configuration, (ii) a second, expanded configuration, and (iii) a density of the plurality of members; and
an elastic member disposed along a region of the structure, the region having a proximal end and a distal end, wherein the elastic member is configured to increase the density within the region by drawing at least one of the proximal and distal ends of the region toward the other of the proximal and distal ends when the structure is in the second configuration.

The vascular device of clause 1, wherein the plurality of spaced members are substantially uniformly spaced.

The vascular device of clause 1, wherein the structure comprises braided strands.

The vascular device of clause 1, wherein the structure comprises a cut metal tube.

The vascular device of clause 1, wherein the structure comprises a tubular stent.

The vascular device of clause 1, wherein, when the structure is in the second configuration, the density within the region is higher than in at least one other portion of the structure.

The vascular device of clause 1, wherein, when the structure is in the second configuration, the density within the region is higher than in an adjacent portion of the structure.

The vascular device of clause 1, wherein, when the structure is in the second configuration, the density within the region is higher than in any other portion of the structure.

The vascular device of clause 1, wherein the elastic member decreases the length of the region by about 10%-40%.

The vascular device of clause 1, wherein the elastic member decreases the length of the region by about 40%-80%.

The vascular device of clause 1, wherein the elastic member comprises an elongate member that is substantially disposed on at least one of an outer surface and an inner surface of the structure.

The vascular device of clause 1, wherein the members form a wall of the structure and the elastic member comprises an elongate member that extends along the wall within the region in a zig-zag pattern.

The vascular device of clause 1, wherein a distal portion of the elastic member wraps around a portion of the first member.

The vascular device of clause 1, wherein the elastic member comprises an enlarged distal end configured to be attached to a portion of the structure.

The vascular device of clause 1, wherein a distal portion of the elastic member is interwoven with a proximal portion of the elastic member.

The vascular device of clause 1, wherein the elastic member comprises an elastic film disposed on at least one of an inner surface and an outer surface of the structure.

The vascular device of clause 16, wherein the elastic film comprises a plurality of pores configured to permit blood to flow therethrough.

The vascular device of clause 16, wherein the elastic film is configured to allow tissue overgrowth thereon.

The vascular device of clause 16, wherein the elastic film forms a substantially cylindrical shape.

The vascular device of clause 16, wherein the elastic film forms a strip.

The vascular device of clause 16, wherein the elastic film is adhered to a portion of the structure within the region.

The vascular device of clause 1, wherein the elastic member comprises an elastic junction extending between intersecting members at an intersection of the members.

The vascular device of clause 22, wherein the junction comprises an elastic adhesive connecting the intersecting members at the intersection.

A method for treating an aneurysm comprising:
positioning a vascular device in a vessel at an ostium of the aneurysm, wherein the device comprises:
a mesh structure formed of a plurality of spaced members, the structure having a density of the plurality of members; and
an elastic member disposed along a region of the structure, the region having a proximal end and a distal end;
expanding the device from a collapsed configuration to an expanded configuration by proximally withdrawing, relative to the device, an outer sheath surrounding the device;
increasing the density within the region by drawing, with the elastic member, at least one of the proximal and distal ends of the region toward the other of the proximal and distal ends as the structure expands to the expanded configuration.

The method of clause 24, wherein the plurality of spaced members are substantially uniformly spaced.

The method of clause 24, wherein the positioning comprises offsetting the region from the ostium of the aneurysm prior to expanding the device.

The method of clause 24, further comprising repositioning the device to center the region along a length of the ostium of the aneurysm while expanding the device.

The method of clause 24, wherein the members form a structure wall and the elastic member comprises an elongate member that extends along the wall within the region in a zig-zag pattern.

The method of clause 24, wherein the elastic member comprises an elastic film disposed on at least one of an inner surface and an outer surface of the structure.

The vascular device of clause 24, wherein the elastic member comprises an elastic junction extending between intersecting members at an intersection of the members.

The vascular device of clause 30, wherein the junction comprises an elastic adhesive connecting the intersecting members at the intersection.

The method of clause 24, wherein the increasing the density of the region comprises reducing a density of at least one of a distal portion or a proximal portion of the structure.

The method of clause 24, wherein the increasing the density of the region comprises moving at least one of a distal end and a proximal end of the structure toward the region.

The method of clause 24, wherein the increasing the density of the region comprises making the region more dense than at least one other portion of the structure.

The method of clause 24, wherein the increasing the density of the region comprises making the region more dense than an adjacent portion of the structure.

The method of clause 24, wherein the increasing the density of the region comprises making the region more dense than any other portion of the structure.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

A detailed description will be made with reference to the accompanying drawings.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology.

Aneurysms may be located, for example, along vessel side walls. A neck of an aneurysm typically defines an opening of between about 2 to 25 mm in length, though other sizes and ranges are also possible. The neck connects an anatomical lumen to a fundus of the aneurysm. In some embodiments, "vessel" or "lumen" may refer to blood vessels (including arteries and veins) or other suitable body organs having a lumen, such as the gastrointestinal tract (e.g., esophagus, stomach, small intestine, colon, rectum), bile ducts, urinary bladder, ureter, urethra, trachea, bronchi, and the like. Blood flow within the anatomical lumen is channeled through the neck and into the fundus. In response to the constant blood flow into the fundus of the aneurysm, the wall of the aneurysm continues to distend and presents a significant risk of rupturing. When the blood within the aneurysm causes pressure against the wall of the aneurysm that exceeds the wall strength, the aneurysm ruptures.

Figure 1A:
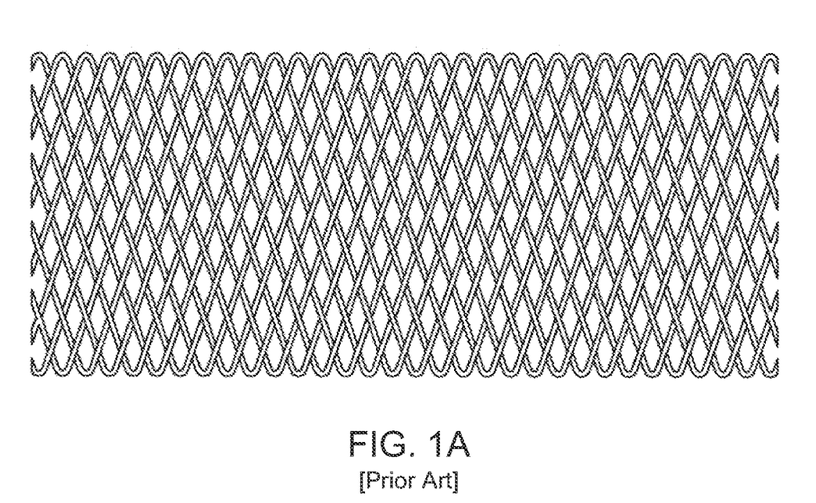
FIG. 1A depicts a side view of a medical device.

Reduction of blood flow to or within the aneurysm results in a reduction in force against the wall of the aneurysm and a corresponding reduction in the risk of rupturing. Conventionally, a reduction of the force and volume of blood entering the aneurysm may be accomplished by an occluding device. FIG. 1A depicts a conventional occluding device as known in the prior art. The conventional occluding device may be dependent on a physician's skill during deployment, to ensure that a desired density (porosity) is attained at the neck of the aneurysm. If the density is too low (porosity too high) at the neck, then the occluding device will fail in sufficiently reducing the blood flow into the fundus. The density of the conventional occluding device may be increased by applying a longitudinally compressive force to a proximal portion of the occluding device towards the direction of a distal portion. Because the density of the occluding device may be modified by application of the compressive force, achieving the desired density (porosity) consistently and reliably is heavily dependant on physician skill.

The medical devices of the subject technology solves some or all of the foregoing problems by occluding blood flow into the aneurysm consistently and reliably, to thereby prevent or reduce likelihood of aneurysm ruptures. The medical devices include a mesh structure formed of a plurality of spaced members and an elastic member disposed along a region of the structure. The elastic member is configured to increase the density (decrease the porosity) of the structure by drawing at least one of the proximal and distal ends of the region toward the other. Accordingly, deployment of the medical device reduces or stops the blood flow into the aneurysm, thereby allowing the blood within the aneurysm to begin to stagnate. Stagnation of blood, as opposed to continuous flow through a fundus of the aneurysm, results in thrombosis in the aneurysm, which also helps protect the aneurysm from rupturing.

Figure 1B:
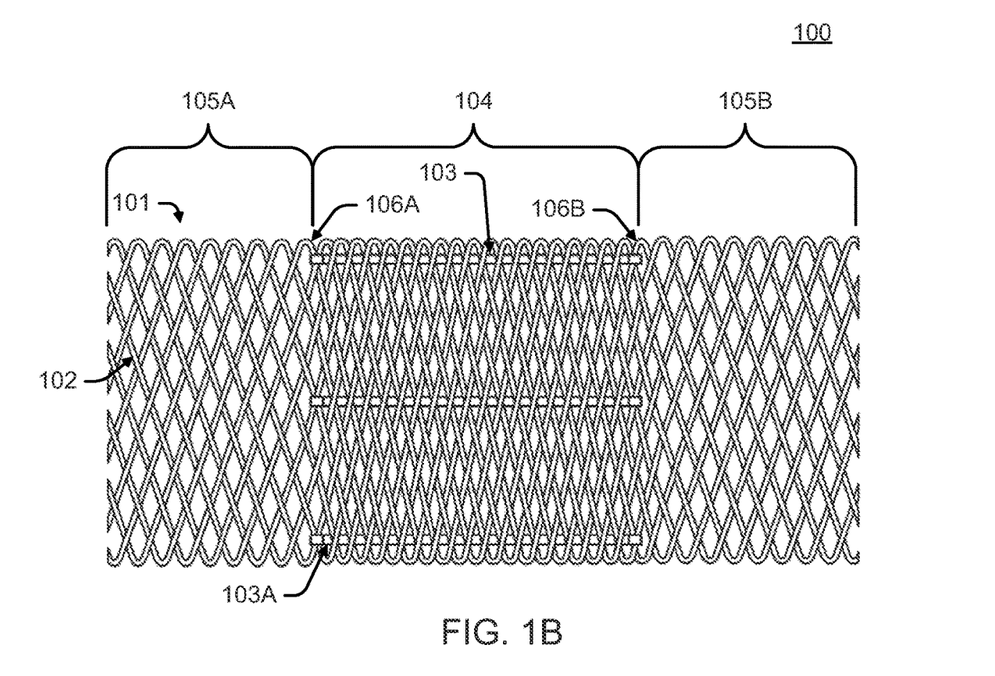
FIG. 1B depicts a side view of a medical device with an elastic member, according to some embodiments of the subject technology.

FIG. 1B depicts a medical device 100 with an elastic member 103, according to some embodiments of the subject technology. The medical device 100 includes a mesh structure 101 formed of a plurality of spaced members 102 and an elastic member 103 disposed along a region of the structure 101. As shown in FIG. 1B, in one aspect, the plurality of spaced members 102 may be substantially uniformly spaced from each other. The medical device 100 may be characterized as a vascular occluding device and/or a pipeline embolization device.

The structure 101 is configured to be axially shortened during and/or after diametrical expansion, with an associated increase in a density (decrease in porosity) of the structure 101 as a result of the axial shortening. The structure 101 may be a self-expanding stent made of two or more round or ovoid wire filaments 102. Accordingly, the structure 101 has a first, collapsed configuration, and a second, expanded configuration. The filaments 102 may be formed of known flexible materials including shape memory materials such as nitinol, platinum and stainless steel. The structure 101 may be fabricated from platinum/8% tungsten and 35N LT (cobalt nickel alloy, which is a low titanium version of MP35N alloy) alloy wires. In other embodiments, one or more of the filaments 102 can be formed of a biocompatible metal material or a biocompatible polymer. The filaments 102 may be braided into a resulting lattice-like structure. In at least one embodiment, during braiding or winding of the structure 101, the filaments 102 may be loosely braided in a 1-over-2-under-2 braiding pattern. In other embodiments, however, other methods of braiding may be followed, without departing from the scope of the disclosure.

Alternatively, the structure 101 may be formed, for example, by laser cutting a pre-formed tube or sheet, by interconnecting a multitude of members 102 by laser welding, or by other suitable methods such as electrochemical etching, grinding, piercing, electroforming, or other means. In another example, the structure 101 may comprise a tubular stent.

The structure 101 has a density (porosity) configured to reduce haemodynamic flow into, for example, an aneurysm. The density of the structure 101, determined by the plurality of members 102, may be adjusted by axially shortening the structure 101. The ends of the structure 101 may be cut to length and therefore remain free for radial expansion and contraction. The structure 101 may exhibit a high degree of flexibility due to the materials used, the density of the structure 101, and the fact that the ends are not secured.

The elastic member 103 may comprise a material having elastic properties capable of being elongated, stretched or deformed and having a restoring force capable of returning the elastic member 103 to its original state.

The elastic member 103 may be disposed along a region 104 of the structure 101. A proximal end of the region 104 may be defined by a first member 106A of the plurality of members 102 and a distal end of the region 104 may be defined by a second member 106B of the plurality of members 102. In one aspect, because the structure 101 may be formed of braided filaments 102, the first member 106A may comprise a proximal portion of a filament and the second member 106B may comprise a distal portion of the same filament. In other words, the first and second members 106A, 106B may comprise different portions of the same member 102. The elastic member may extend between the first and second members 106A, 106B to thereby increase the density within the region 104 by drawing at least one of the proximal and distal ends of the region 104 toward the other of the proximal and distal ends when the structure 101 is in the second, expanded configuration. By drawing the proximal and distal ends of the region 104 toward the other, the axial length of the region 104 is shortened, thereby increasing the density of the region 104. For example, the elastic member 103 may decrease the axial length of the region 104 by about 10%-40% for some applications, and about 40%-80% in other applications. For example, if it is desired to provide minimal blood flow into an aneurysm sac, the elastic member 103 may be configured to decrease the axial length of the region 104 by about 10%-40%. On the other hand, if it is desired to have a highly dense region 104 to substantially prevent blood flow into an aneurysm sac, the elastic member 103 may be configured to decrease the axial length of the region 104 by about 40%-80%.

In one aspect, the elastic member 103 may decrease the axial length of the region 104 without substantially changing the diameter of the structure 101. For example, the elastic member 103 may decrease the axial length of the region 104 between about 10% and about 40% while the diameter of the structure 101 changes by less than about 2% for a decrease in axial length of about 10% and less than about 8% for a decrease in axial length of about 40%. In one aspect, the medical devices 100 may be configured with regions 104 having different axial lengths. A physician may select the appropriate medical device 100 based on a size of the neck of the aneurysm and the axial length of the region 104.

When the structure 101 is in the second, expanded configuration, the elastic member 103 causes the density within the region 104 to be higher than a density in the proximal portion 105A and/or the distal portion 105B of the structure 101. In one aspect, the elastic member 103 causes the density within the region 104 to be higher than a density in an adjacent portion of the structure 101. In another aspect, the elastic member 103 causes the density within the region 104 to be higher than a density in any other portion of the structure 101.

Referring to FIG. 1B, in one example, the elastic member 103 may comprise an elongate member 103A that is substantially disposed on at least one of an outer surface and an inner surface of the structure 101. As stated above, the elongate member 103A may extend between the first and second members 106A, 106B to thereby increase the density within the region 104 by drawing at least one of the proximal and distal ends of the region 04 toward the other of the proximal and distal ends when the structure 101 is in the second, expanded configuration.

Figure 2A:
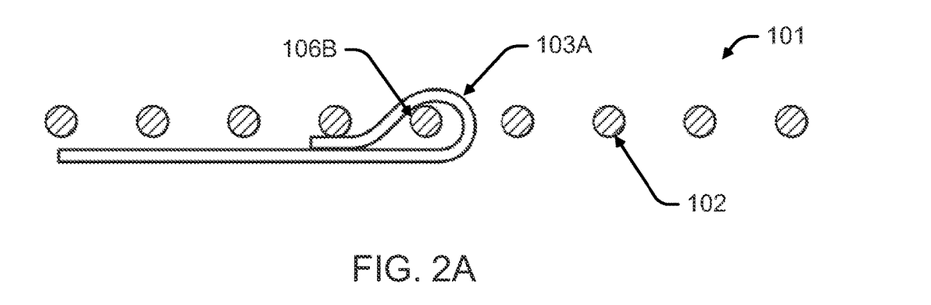
FIG. 2A depicts a partial cross section of a medical device and an elastic member, according to some embodiments of the subject technology.
Figure 2B:
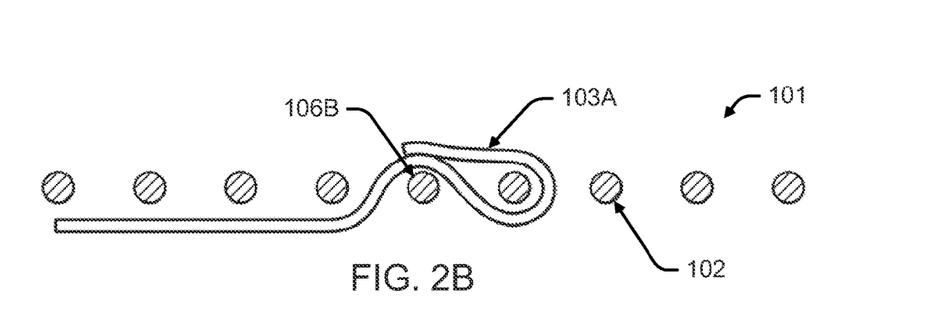
FIG. 2B depicts a partial cross section of a medical device and an elastic member, according to some embodiments of the subject technology.

FIGS. 2A and 2B depict a partial cross section of the medical device 100 and the elastic member 103A, according to some embodiments of the subject technology. Each distal portion of the elongate member 103A may be wound or wrapped around a portion of the first member 106A or the second member 106B. In one aspect, the distal portions of the elongate member 103A are wound around the first or second members 106A, 106B and then attached to a portion of the elongate member 103A by, for example, heat fusion. In another aspect, the distal portions of the elongate member 103A are wound around the first or second members 106A, 106B and then attached to the structure 101 by, for example, heat fusion.

Figure 3:
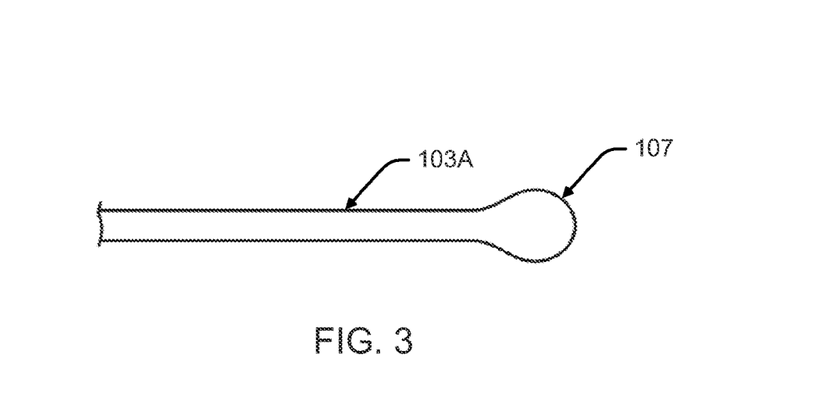
FIG. 3 depicts a top view of a distal portion of an elastic member, according to some embodiments of the subject technology.

FIG. 3 depicts a distal portion of the elastic member 103A, according to some embodiments of the subject technology. To facilitate the bonding of the distal portions with the portion of the elongate member 103A or the structure 101, the elongate member 103A may comprise an enlarged distal end 107. The enlarged distal end 107 may be configured to be attached to a portion of the elongate member 103A or the structure 101 by having sufficient contact area to permit a strong fusion bond.

Referring to FIG. 1B, in one aspect, the medical device 100 may comprise two or more elongate members 103A. For example, the elongate members 103A may be disposed circumferentially around the structure 101. The elongate members 103A may be equally spaced or clustered at a particular area of the structure 101. For example, two or more elongate members 103A may be disposed on an upper half of the structure, while a lower half has one or less elongate member 103A. Accordingly, it will be appreciated that any number of elongate members 103A may be employed without departing from the scope of the disclosure.

Figure 4:
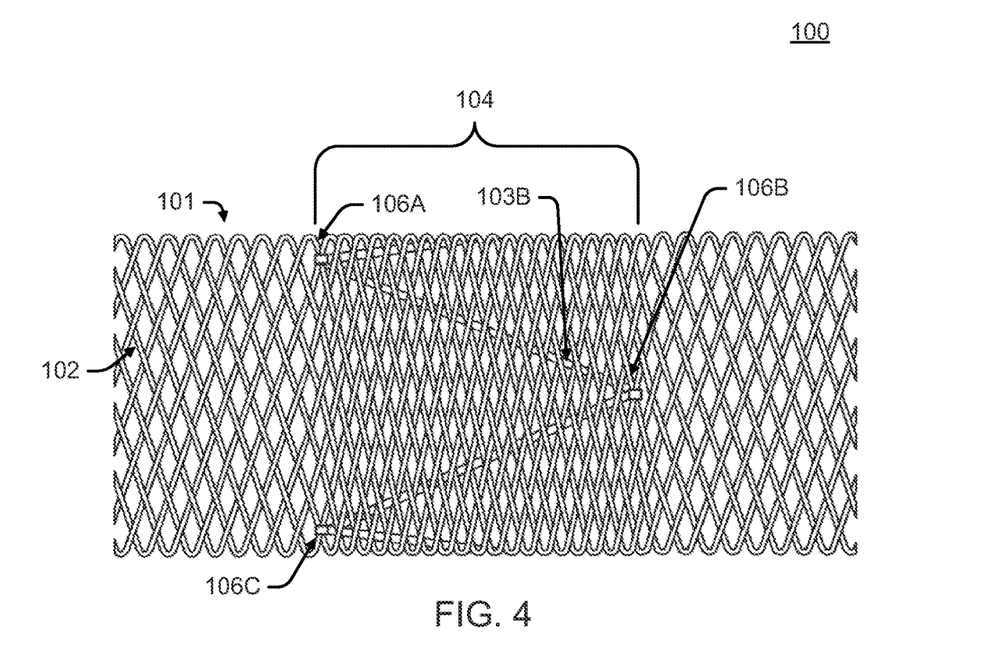
FIG. 4 depicts a side view of a medical device with an elastic member, according to some embodiments of the subject technology.

FIG. 4 depicts the medical device 100 with an elastic member 103B, according to some embodiments of the subject technology. The members 102 form a wall of the structure 101. In this example, the elastic member 103 may comprise an elongate member 103B that extends along the wall within the region 104 in a zig-zag pattern. For example, the elongate member 103B may extend between the first and second members 106A, 106B and alternate between the second and a third member 106B, 106C. The elongate member 103B may continue to alternate circumferentially around the structure 101 in a zig-zag pattern until it contacts the first member 106A. In one aspect, because the structure 101 may be formed of braided filaments 102, the first member 106A may comprise a proximal portion of a filament, the second member 106B may comprise an intermediate portion of the same filament, and the third member 106C may comprise a distal portion of the same filament. In other words, the first, second, and third members 106A, 106B, 106C may comprise different portions of the same member 102. The zig-zag elongate member 103B increases the density within the region 104 by drawing at least one of the proximal and distal ends of the region 104 toward the other of the proximal and distal ends when the structure 101 is in the second, expanded configuration.

The elongate member 103B may be wound or wrapped around a portion of the corresponding member 106A, 106B, 106C. In one example, the distal portion of the elongate member 103B are wound around the corresponding member 106A, 106B, 106C and then attached to a portion of the elongate member 103B by, for example, heat fusion. In another example, the distal portion of the elongate member 103B may be wound around the corresponding member 106A, 106B, 106C and then attached to the structure 101 by, for example, heat fusion.

Figure 5:
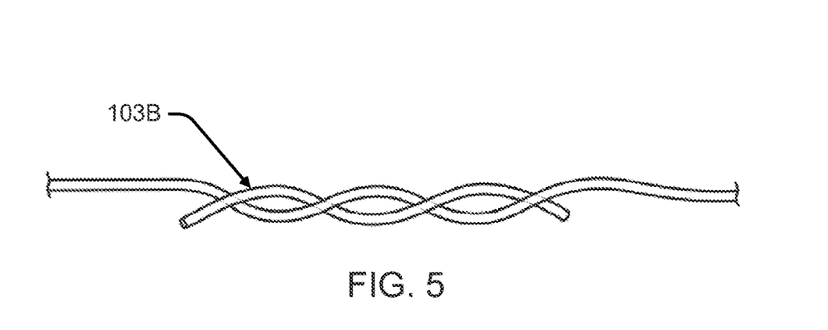
FIG. 5 depicts a proximal and distal portion of an elastic member, according to some embodiments of the subject technology.

FIG. 5 depicts a proximal and distal portion of the elastic member 103B, according to some embodiments of the subject technology. The distal portion of the elongate member 103B may be interwoven with a proximal portion of the elongate member 103B. In this example, the ends of the elongate member 103B may be interweaved with one another and secured to each other using heat fusion, adhesives, or other means.

Figure 6:
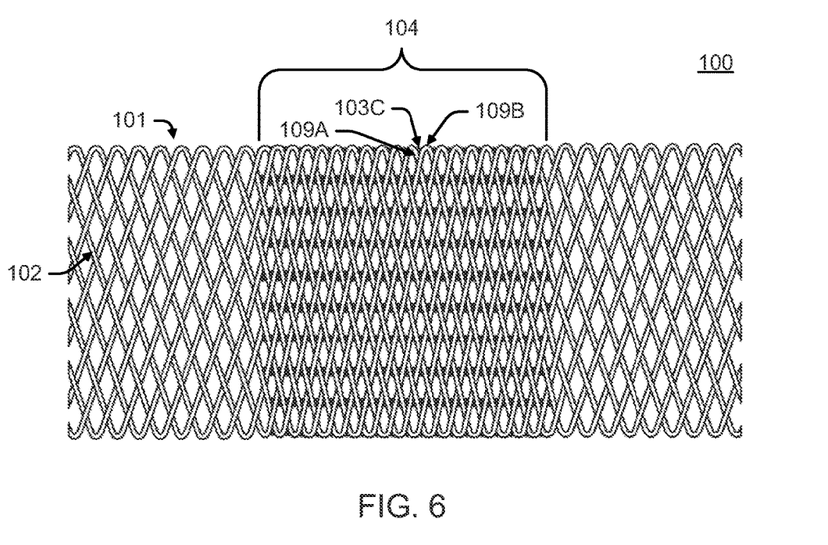
FIG. 6 depicts a side view of a medical device with an elastic member, according to some embodiments of the subject technology.

FIG. 6 depicts the medical device 100 with an elastic member 103C, according to some embodiments of the subject technology. In this example, the elastic member 103 may comprise an elastic junction 103C extending between intersecting members 109A, 109B at an intersection 108 of the members 102. The elastic junction 103C may comprise an elastic adhesive that connects the intersecting members 109A, 109B and is disposed at the intersection 108. The elastic adhesive may be silicone, polyurethane, or other materials having highly elastic mechanical properties. The elastic junction 103C may be disposed at multiple intersections 108, thereby defining the region 104.

Figure 7A:
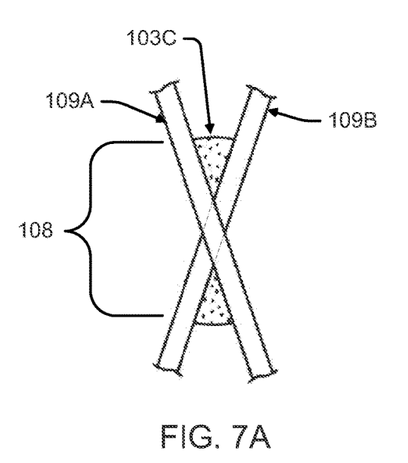
FIG. 7A depicts an elastic junction at rest, according to some embodiments of the subject technology.
Figure 7B:
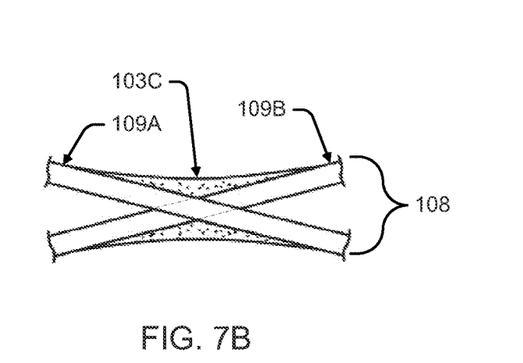
FIG. 7B depicts an elastic junction in a stretched configuration, according to some embodiments of the subject technology.

FIGS. 7A and 7B depict the elastic junction 103C at rest and in a stretched configuration, respectively, according to some embodiments of the subject technology. The elastic junctions 103C increase the density within the region 104 by shortening the axial length of the region 104 due to an elastic force of each elastic junction 103C. For example, at rest, each elastic junction 103C is configured to pull the intersecting members 109A, 109B toward each other. When the intersecting members 109A, 109B are stretched or pulled apart, the elastic junction 103C is configured to pull the intersecting members 109A, 109B toward each other. Accordingly, when the medical device 100 is in collapsed configuration, the elastic junction 103C is in the stretched configuration, as shown in FIG. 7B. When the medical device is in the expanded configuration, the elastic junction 103C is substantially at rest.

Figure 8:
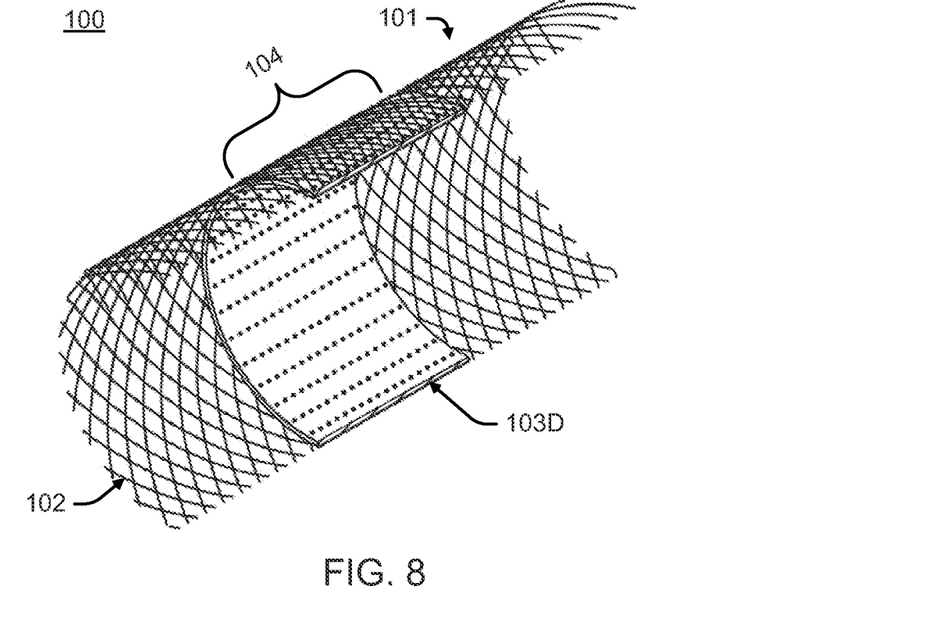
FIG. 8 depicts an isometric cut away of a medical device with an elastic member, according to some embodiments of the subject technology.
Figure 9:
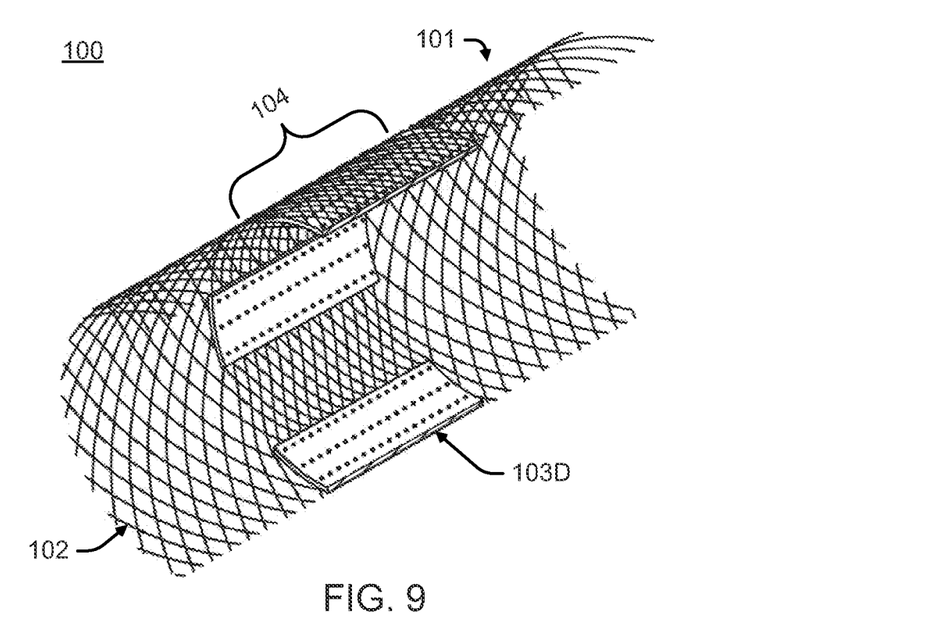
FIG. 9 depicts an isometric cut away of a medical device with an elastic member, according to some embodiments of the subject technology.

FIGS. 8 and 9 depict the medical device 100 with an elastic member 103D, according to some embodiments of the subject technology. In this example, the elastic member 103 may comprise an elastic film 103D. The elastic film 103D may comprise silicone, polyurethane or other materials having highly elastic mechanical properties. The elastic film 103D may be disposed on at least one of an inner surface and an outer surface of the structure 101, the area of the structure 101 covered by the elastic film 103D thereby being the region 104. In one example, the elastic film 103D may be applied to both, the inside surface of the structure 101 and the outside surface of the structure 101. In one aspect, the elastic film 103D may comprise a plurality of pores configured to permit blood to flow therethrough. For example, each pore of the plurality of pores may have a diameter of about 70-200 µm. In another aspect, the elastic film 103D may be configured to prevent blood to flow therethrough. In yet another aspect, the elastic film 103D may be configured to allow or facilitate tissue overgrowth thereon.

The elastic film 103D may be applied circumferentially along the region 104 of the structure 101, thereby forming a substantially cylindrical shape. Alternatively, referring to FIG. 9, the elastic film 103D may be applied to a portion of the region 104 of the structure 101, thereby forming a strip or a semi-cylindrical shape along the longitudinal axis of the structure 101.

In another aspect, the elastic film 103D may be adhered to the structure 101 within the region 104 over a portion or all of its axial length and/or a portion or all of its circumference. The elastic film 103D increases the density within the region 104 by shortening the axial length of the region 104 due to an elastic force of elastic film 103D. The elastic film 103D is applied to the region 104 when the medical device 100 is in the expanded configuration, such that the elastic film 103D is in a stretched configuration when the medical device 100 is in the collapsed configuration.

Radiopaque markers may be located adjacent the proximal or distal portions 105A, 105B or both, and may be located at any position along the length of the medical device 100 between a proximal and distal end of the medical device 100, including the region 104. The markers may be attached to the medical device 100 by techniques such as adhesives, heat fusion, interference fit, fasteners, intermediate members, coatings, or by other techniques.

In some embodiments, the markers are comprised of ultrasonic markers, MRI safe markers, or other markers. In some embodiments ultrasonic markers permit a physician to accurately determine the position of the medical device 100 within a patient under ultrasonic visualization. Materials for an ultrasonic marker have an acoustical density sufficiently different from the medical device 100 to provide suitable visualization via ultrasonic techniques. Exemplary materials comprise polymers, metals such as tantalum, platinum, gold, tungsten and alloys of such metals, hollow glass spheres or microspheres, and other materials.

In some embodiments, MRI safe markers permit a physician to accurately determine the position of the medical device 100 within a patient under magnetic resonance imaging. Exemplary materials for making MRI safe marker have a magnetic signature sufficiently different from the medical device 100 to provide suitable visualization via MRI techniques. Exemplary materials comprise polymers, metals such as tantalum, platinum, gold, tungsten and alloys of such metals, non-ferrous materials, and other materials.

Figure 10:
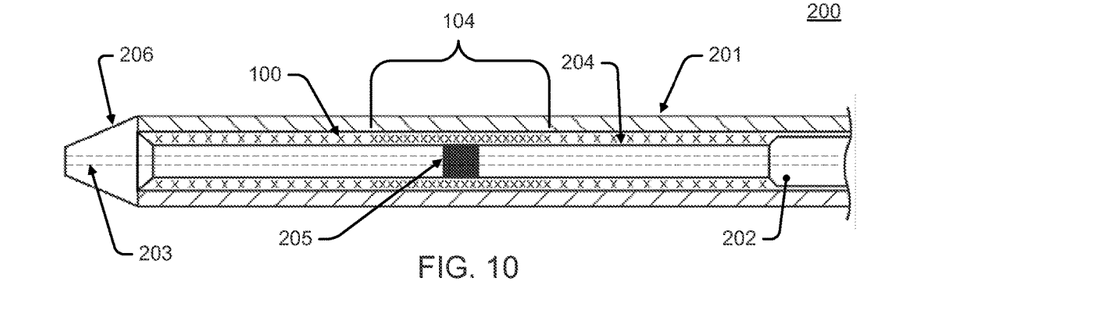
FIG. 10 depicts a cross section view of a medical device and a delivery system, according to some embodiments of the subject technology.

A technique for treating an aneurysm will now be discussed with reference to FIGS. 10-14. Referring to FIG. 10, the medical device 100 may be delivered into a treatment site using a delivery system 200. The delivery system 200 may include an outer sheath 201 and an inner tube 202. The medical device 100 may be disposed and confined within an annular space between the outer sheath 201 and the inner tube 202, in the first, collapsed configuration.

The medical device 100 and the inner tube 202 may be cooperatively movable within the outer sheath 201 in order to deliver the medical device 100 to a treatment site, such as an aneurysm, within the vasculature of a patient.

The outer sheath 201 may be configured to be introduced and advanced through the vasculature of the patient. The outer sheath 201 may be made from various thermoplastics, e.g., PTFE, FEP, HDPE, PEEK, etc., which may optionally be lined on the inner surface of the outer sheath 201 or an adjacent surface with a hydrophilic material such as PVP or some other plastic coating. Additionally, either surface may be coated with various combinations of different materials, depending upon the desired results.

The inner tube 202 includes a guide wire lumen 203 for providing a guide wire to extend therethrough. The inner tube 202 also has a reduced diameter at a distal region 204 to provide sufficient annular space in which the medical device 100 is stowed.

Radiopaque markers may be provided at various locations along the length of the delivery system 200. For example, an enlarged distal tip 206 of the inner tube 202 may be radiopaque. In another example, radiopaque markers may be provided on the reduced diameter distal region 204 of the inner tube 202, beneath the distal and proximal ends of the medical device 100. In yet another example, a radiopaque marker 205 may be disposed on the inner tube 202 adjacent to a longitudinal center of the region 104.

Figure 11:
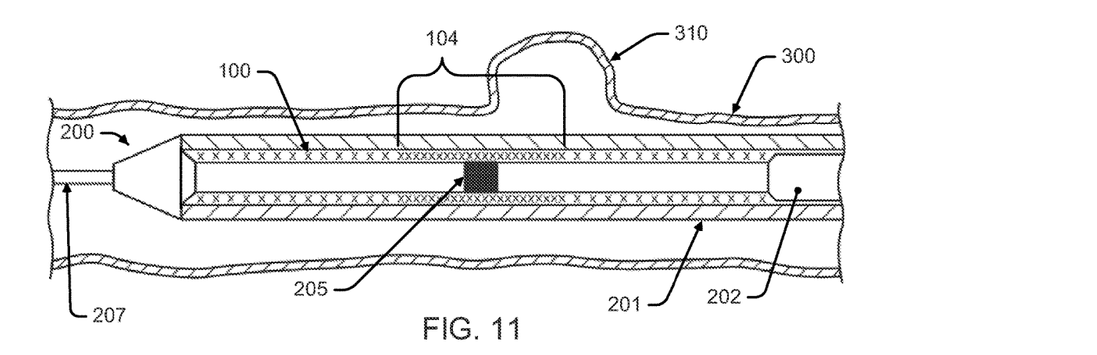
FIG. 11 depicts a cross section view of a vessel and delivery of a medical device according to some embodiments of the subject technology.

Based on the axial length of the region 104 and a length of a neck of the aneurysm, the medical device 100 is selected such that the axial length of the region 104, when the medical device 100 is in the second, expanded configuration, is longer than the length of the neck of the aneurysm. Referring to FIG. 11, the delivery system 200 is advanced percutaneously over a guidewire 207 to the treatment site, in this example to the site of the aneurysm 310. Specifically, the medical device 100 may be positioned in the vessel 300 at an ostium or the neck of the aneurysm 310. In one aspect, the radiopaque marker 205 may be positioned distal to a distal lateral wall of the aneurysm 310, thereby offsetting the region 104 from the ostium of the aneurysm 310 prior to expanding the medical device 100.

Figure 12:
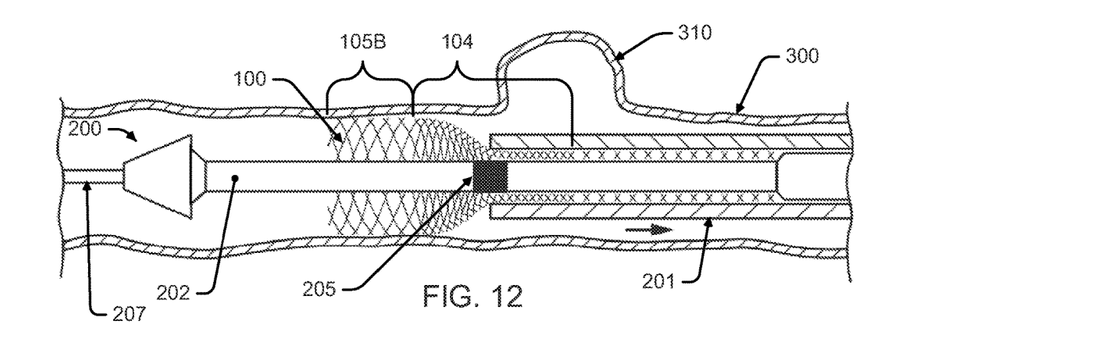
FIG. 12 depicts a cross section view of a vessel and delivery of a medical device according to some embodiments of the subject technology.

Referring to FIG. 12, after navigating the delivery system 200 to the treatment site within the patient, the medical device 100 may be deployed from the outer sheath 201 in a variety of ways. In one embodiment, the outer sheath 201 is withdrawn proximally while maintaining the position of the inner tube 202 to thereby expose a distal portion of the inner tube 202 and the medical device 100. Upon exiting the outer sheath 201, the portion of the medical device 100 that is not situated between the outer sheath 201 and the inner tube 202 begins to simultaneously axially shorten and radially self expand until the medical device 100 contacts the luminal wall of the vessel 300.

The outer sheath 201 is only withdrawn until a distal end of outer sheath 201 is axially aligned with the radiopaque marker 205. The elastic member 103 maintains the density within the region 104 during expansion of the medical device 100 such that the density within the region 104 is higher then the density in the distal portion 105B or an adjacent portion of the structure 101.

Figure 13:
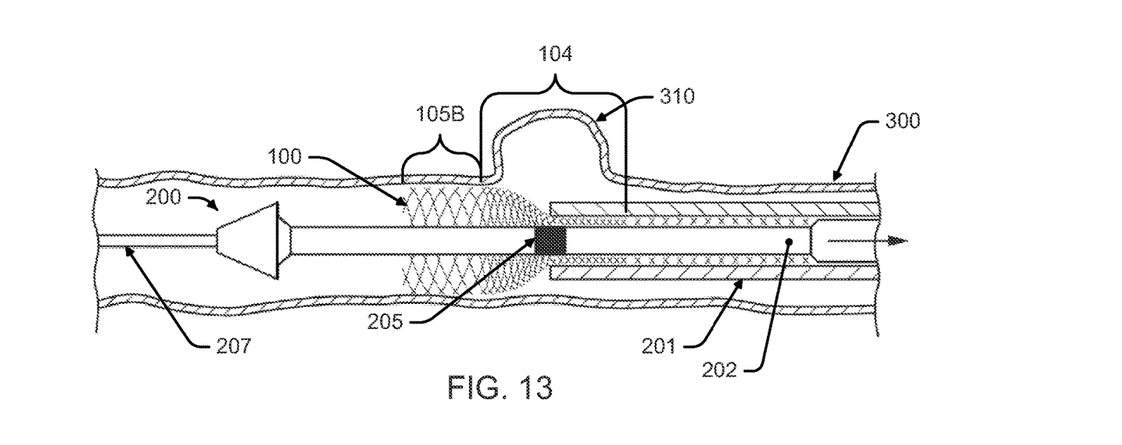
FIG. 13 depicts a cross section view of a vessel and delivery of a medical device according to some embodiments of the subject technology.

Referring to FIG. 13, the delivery system 200 is withdrawn proximally until the radiopaque marker 205 is centered along the length of the ostium or neck of the aneurysm 310. In other words, after the medical device 100 has been repositioned such that the region 104 is centered along the length of the ostium, the region 104 will cover the ostium or neck of the aneurysm 310 when the medical device 100 is in the second, expanded configuration. Accordingly, even though the density of the region 104 may be reduced when the medical device is in the first, collapsed configuration (due to stretching of the medical device 100), the elastic member 103 causes the region 104 to achieve a density that is higher than a density of other portions of the structure 101 after the medical device 100 is in the second, expanded configuration.

As discussed above and in reference to FIG. 1, the elastic member 103 increases the density within the region 104 by drawing, with the elastic member 103, at least one of the proximal and distal ends of the region 104 toward the other of the proximal and distal ends when the structure 101 is in the expanded configuration. In another aspect, the elastic member 103 may cause the axial length of the region to be shortened (thereby increasing the density of the region 104), by reducing the density of adjacent portions of the structure 101. For example, the elastic member 103 may reduce the density of the proximal or distal regions 105A, 105B of the structure 101 by elongating the proximal or distal regions 105A, 105B due to movement of the proximal or distal regions 105A, 105B towards the region 104. In this example, a proximal or distal end of the structure 101 would be anchored against the inner wall of the vessel 300 and thus, movement of the proximal or distal regions 105A, 105B toward the region 104 causes the proximal or distal regions 105A, 105B to elongate, thereby reducing the density of the proximal or distal regions 105A, 105B.

In another aspect, the elastic member 103 may increase the density within the region 104 by moving at least one of the distal end and the proximal end of the structure 101 toward the region.

The elastic member 103 thereby causes the region 104 to return to a pre-programmed density regardless of the endless variety of physician induced movements that can occur during the deployment of the medical device 100. Stated another way, the density of the region 104 is relatively insensitive to physician applied motions during deployment of the medical device 100.

Figure 14:
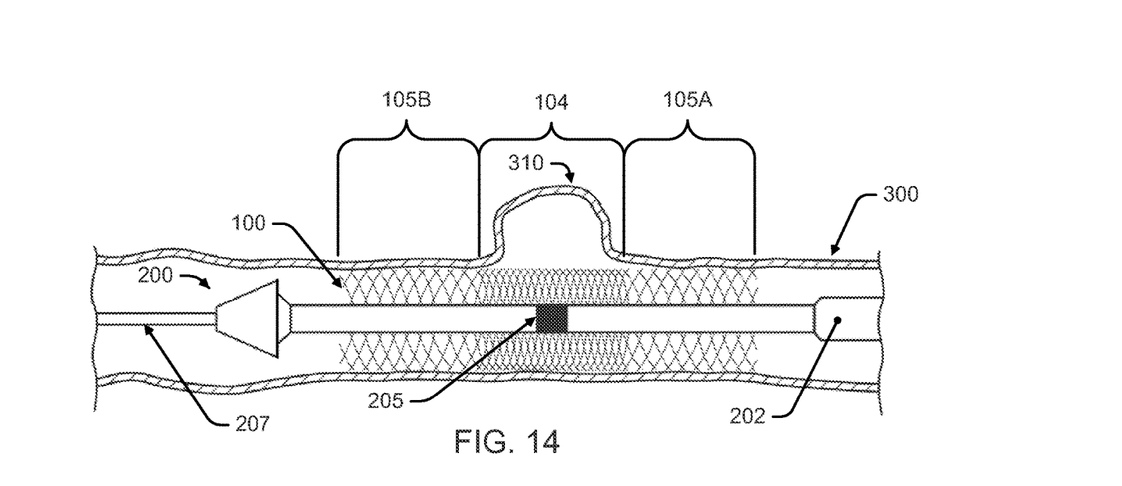
FIG. 14 depicts a cross section view of a vessel and delivery of a medical device according to some embodiments of the subject technology.

Referring to FIG. 14, the outer sheath 201 may then be further withdrawn proximally to expose the medical device 100 and allow the medical device 100 to fully deploy. Once the entire medical device 100 is expanded, the outer sheath 201 and the inner tube 202 may be withdrawn from the body.

The region 104 of the medical device 100 has a significantly higher density compared to other portions of the structure 101. Due to the higher density of the region 104, less blood flows into the aneurysm 310 such that substantial thrombosis may occur within the aneurysm 310.

In one arrangement, the medical device 100 may be comprised of metal, polymer, ceramic, permanent enduring materials, and may comprise either of or both of non-bioabsorbable and bioabsorbable materials. Exemplary materials include, but are not limited to, NITINOL®, stainless steel, cobalt chromium alloys, Elgiloy, magnesium alloys, polylactic acid, poly glycolic acid, poly ester amide (PEA), poly ester urethane (PEU), amino acid based bio-analogous polymers, tungsten, tantalum, platinum, polymers, bio-polymers, ceramics, bio-ceramics, or metallic glasses. Part or all of the medical device may elute over time substances such as drugs, biologics, gene therapies, anti-thrombotics, coagulants, anti-inflammatory drugs, immuno-modulator drugs, anti-proliferatives, migration inhibitors, extracellular matrix modulators, healing promoters, re-endothelialization promoters, or other materials. In some embodiments, the medical device 100 may be formed from materials having shape memory properties. In some embodiments, the medical device 100 may be finished by processes to remove slag. In some embodiments, the medical device 100 may be subjected to a tempering treatment at temperatures customarily applied to the material so that the impressed structure is permanently established.

The medical device 100 may have various lengths and diameters. For example, the medical device 100 may have specific cross-sectional diameters, the diameters being measured when the medical device 100 is fully free to expand, ranging from about 2 mm to about 6 mm. If the medical device 100 has a diameter between 3 mm and 4 mm, it may be used in size 021 microcatheters. If the medical device 100 has a diameter between 5 mm and 6 mm, it may be used in size 027 microcatheters. However, other suitable cross-sectional diameters may be used without deviating from the scope of the subject technology. In some embodiments, the medical device 100 may have lengths, measured proximally to distally along the longitudinal axis of the medical device 100, ranging from 15 mm to 40 mm, though other ranges and sizes are also possible.

Skilled artisans may implement the described functionality in varying ways for each particular application. Various components and blocks may be arranged differently (for example, arranged in a different order, or partitioned in a different way) all without departing from the scope of the subject technology. It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (for example, his) include the feminine and neuter gender (for example, her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "aspect" does not imply that such aspect is essential to the subject technology or that such aspect applies to all configurations of the subject technology. A disclosure relating to an aspect may apply to all aspects, or one or more aspects. An aspect may provide one or more examples. A phrase such as an "aspect" may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A vascular device, comprising:
   a mesh structure formed of a plurality of spaced members, the structure having (i) a first, collapsed configuration, (ii) a second, expanded configuration, and (iii) a density of the plurality of members; and
   an elastic film disposed circumferentially along an inner surface of a region of the structure, thereby forming a substantially cylindrical shape along the inner surface, the region having a proximal end and a distal end, wherein the elastic film is (i) attached to the proximal end and the distal end and (ii) configured to increase the density within the region by drawing at least one of the proximal and distal ends of the region toward the other of the proximal and distal ends when the structure is in the second configuration.

2. The vascular device of claim 1, wherein the elastic film comprises a plurality of pores configured to permit blood to flow therethrough.

3. The vascular device of claim 2, wherein the pores are sized between about 70-200 microns.

4. The vascular device of claim 1, wherein the elastic film is configured to decrease the length of the region by about 10%-40% in the second configuration.

5. The vascular device of claim 1, wherein the elastic film is configured to allow tissue overgrowth thereon.

6. The vascular device of claim 1, wherein the elastic film is adhered to a portion of the structure within the region.

7. The vascular device of claim 1, wherein the elastic film is configured to decrease an axial length of the region without substantially changing a cross-sectional dimension of the structure.

8. The vascular device of claim 1, wherein the elastic film comprises silicone or polyurethane.

9. The vascular device of claim 1, wherein the elastic film extends across the entire inner surface of the region.

10. The vascular device of claim 1, further comprising a second elastic film disposed along an outer surface of the region of the structure.

11. A method for treating an aneurysm comprising:
    positioning the vascular device of claim 1 in a vessel at an ostium of the aneurysm,
    expanding the device from a collapsed configuration to an expanded configuration by proximally withdrawing, relative to the device, an outer sheath surrounding the device;
    increasing the density within the region by drawing, with the elastic film, at least one of the proximal and distal ends of the region toward the other of the proximal and distal ends as the structure expands to the expanded configuration.

12. The method of claim 11, wherein the elastic film comprises a plurality of pores configured to permit blood to flow therethrough.

13. The method of claim 11, wherein the elastic film is configured to decrease the length of the region by about 10%-40% in the expanded configuration.

14. The method of claim 11, wherein the elastic film is configured to allow tissue overgrowth thereon.

15. The method of claim 11, wherein the elastic film is adhered to a portion of the structure within the region.

* * * * *